(12) United States Patent
Bold et al.

(10) Patent No.: US 7,795,288 B2
(45) Date of Patent: Sep. 14, 2010

(54) THIAZOLE AND PYRAZOLE DERIVATIVES AS FLT-3 KINASE INHIBITORS

(75) Inventors: Guido Bold, Gipf-Oberfrick (CH); Andreas Floersheimer, Dornach (CH); Pascal Furet, Thann (FR); Vito Guagnano, Basel (CH); Keiichi Masuya, Ibaraki (JP); Andrea Vaupel, Riehen (CH); Joseph Schoepfer, Riehen (CH)

(73) Assignee: Novartis AG, Basel (CH)

( * ) Notice: Subject to any disclaimer, the term of this patent is extended or adjusted under 35 U.S.C. 154(b) by 909 days.

(21) Appl. No.: 10/578,826

(22) PCT Filed: Nov. 12, 2004

(86) PCT No.: PCT/EP2004/012892
§ 371 (c)(1),
(2), (4) Date: Nov. 20, 2006

(87) PCT Pub. No.: WO2005/047273
PCT Pub. Date: May 26, 2005

(65) Prior Publication Data
US 2007/0167449 A1    Jul. 19, 2007

(30) Foreign Application Priority Data
Nov. 14, 2003 (GB) .................. 0326601

(51) Int. Cl.
*A61K 31/426* (2006.01)
*C07D 277/20* (2006.01)

(52) U.S. Cl. .............. 514/370; 548/146; 548/190; 548/193; 544/358; 544/367; 514/365; 514/252.13; 514/254.02

(58) Field of Classification Search .............. 544/336, 544/358, 359, 367; 548/146, 190, 193; 514/252.12, 514/252.13, 254.02, 365, 370
See application file for complete search history.

(56) References Cited

U.S. PATENT DOCUMENTS

| | | | | |
|---|---|---|---|---|
| 4,612,321 | A * | 9/1986 | Terao et al. | 514/338 |
| 4,649,146 | A * | 3/1987 | Takaya et al. | 514/307 |
| 4,735,957 | A * | 4/1988 | Takaya et al. | 514/342 |
| 6,620,825 | B1 * | 9/2003 | Ohkawa et al. | 514/340 |

OTHER PUBLICATIONS

Takaya et al (1985): STN International HCAPLUS database, (Columbus, Ohio), Accession No. 1985:45931.*

* cited by examiner

*Primary Examiner*—Golam M Shameem

(57) ABSTRACT

The invention relates to thiazole and pyrazole derivatives of formula (I) wherein Q is S and X is C, or Q is CH and X is N; $R_1$ is unsubstituted or substituted phenyl; and $R_2$ is unsubstituted or substituted aryl or heteroaryl; or a salt of the said compounds, and to processes for the preparation thereof, to pharmaceutical compositions comprising such derivatives and to the use of such derivatives for the preparation of pharmaceutical compositions for the treatment especially of a proliferative disease, such as a tumour disease, in particular such diseases which respond to an inhibition of the Flt-3 kinase.

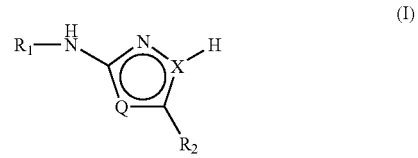

(I)

6 Claims, No Drawings

THIAZOLE AND PYRAZOLE DERIVATIVES AS FLT-3 KINASE INHIBITORS

This application is the National Stage of Application No. PCT/EP2004/012892, filed on Nov. 12, 2004. The contents of both are incorporated herein by reference in their entirety.

The invention relates to thiazole and pyrazole derivatives and to processes for the preparation thereof, to pharmaceutical compositions comprising such derivatives and to the use of such derivatives for the preparation of pharmaceutical compositions for the treatment especially of a proliferative disease, such as a tumour disease, in particular such diseases which respond to an inhibition of the Flt-3 kinase.

The invention relates to thiazole and pyrazole derivatives of formula I

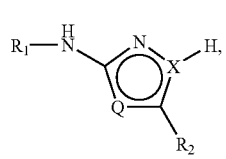

wherein

Q is S and X is C, or

Q is CH and X is N;

$R_1$ is unsubstituted or substituted phenyl; and $R_2$ is unsubstituted or substituted aryl or heteroaryl;

or a salt of the said compounds.

The general terms used hereinbefore and hereinafter preferably have, within this disclosure, the following meanings, unless otherwise indicated:

Where the plural form is used for compounds, salts, pharmaceutical preparations, diseases and the like, this is intended to mean also a single compound, salt, or the like.

Where compounds of formula I are mentioned which can form tautomers, it is meant to include also the tautomers of such compounds of formula I.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

Salts are preferably the pharmaceutically acceptable salts of compounds of formula I if they are carrying salt-forming groups.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxy-ethyl)-amine, or heterocyclic bases, for example N-ethyl-piperidine or N,N'-dimethyl-piperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

Asymmetric carbon atoms of a compound of formula I that are optionally present may exist in the (R), (S) or (R,S) configuration, preferably in the (R) or (S) configuration. Substituents at a double bond or a ring may be present in cis- (=Z-) or trans (=E-) form. The compounds may thus be present as mixtures of isomers or preferably as pure isomers.

In $R_1$ being substituted phenyl, the phenyl group is preferably substituted by one or more, especially by one or two, radical(s) selected from the group consisting of hydroxy, lower alkyl, halogen-lower alkyl, lower alkoxy, pyrrolidinyl-lower alkoxy wherein the pyrrolidinyl moiety is optionally substituted by lower alkyl, piperidinyl-lower alkoxy, morpholinyl-lower alkoxy, N,N-di-lower alkylamino-lower alkyl, N,N-di-lower alkylamino-lower alkoxy and lower alkyl-piperazinyl.

Unsubstituted or substituted aryl $R_2$ is preferably phenyl that is optionally substituted by one or more, especially by one, radical(s) selected from the group consisting of halo, hydroxy, lower alkoxy and N,N-di-lower alkylamino-lower alkoxy.

Unsubstituted or substituted heteraryl $R_2$ is preferably thiophenyl that is optionally substituted by one or more, especially by one, radical(s) selected from the group consisting of halo, hydroxy, lower alkoxy and N,N-di-lower alkylamino-lower alkoxy. Most preferably it is unsubstituted thiophenyl.

$R_2$ is most preferably thiophenyl.

The prefix "lower" denotes a radical having 1 up to and including a maximum of 7, especially 1 up to and including a maximum of 4 carbon atoms, the radicals in question being either linear or branched with single or multiple branching. Lower alkyl, for example, is methyl, ethyl, n-propyl, sec-propyl, n-butyl, isobutyl, sec-butyl, tert-butyl, n-pentyl, n-hexyl or n-heptyl.

Halo(geno) is preferably iodo, bromo, chloro or fluoro, especially fluoro, chloro or bromo.

The compounds of formula I have valuable pharmacological properties and are useful in the treatment of proliferative diseases, in particular of protein tyrosine kinase dependent, especially Flt-3 dependent, diseases.

The efficacy of the compounds of formula I as inhibitors of Flt-3 protein-tyrosine kinase activity can be demonstrated as follows:

The baculovirus donor vector pFbacG01 (GIBCO) is used to generate a recombinant baculovirus expressing the amino acid region amino acids 563-993 of the cytoplasmic kinase domain of human Flt-3. The coding sequence for the cytoplasmic domain of Flt-3 is amplified by PCR from human c-DNA libraries (Clontech). The amplified DNA fragments and the pFbacG01 vector are made compatible for ligation by digestion with BamH1 and HindIII. Ligation of these DNA fragments results in the baculovirus donor plasmid Flt-3 (1.1). The production of the viruses, the expression of proteins in Sf9 cells and the purification of the GST-fused proteins are performed as follows:

Production of virus: Transfer vector (pFbacG01-Flt-3) containing the Flt-3 kinase domain is transfected into the DH10Bac cell line (GIBCO) and the transfected cells are plated on selective agar plates. Colonies without insertion of the fusion sequence into the viral genome (carried by the bacteria) are blue. Single white colonies are picked and viral DNA (bacmid) is isolated from the bacteria by standard plasmid purification procedures. Sf9 or Sf21 cells (American Type Culture Collection) are then transfected in flasks with the viral DNA using Cellfectin reagent.

Protein expression in Sf9 cells: Virus containing media is collected from the transfected cell culture and used for infection to increase its titre. Virus containing media obtained after two rounds of infection is used for large-scale protein expression. For large-scale protein expression 100 cm$^2$ round tissue culture plates are seeded with $5 \times 10^7$ cells/plate and infected with 1 mL of virus-containing media (approx. 5 MOIs). After 3 days the cells are scraped off the plate and centrifuged at 500 rpm for 5 min. Cell pellets from 10-20, 100 cm$^2$ plates are resuspended in 50 mL of ice-cold lysis buffer (25 mM Tris-HCl, pH 7.5, 2 mM EDTA, 1% NP-40, 1 mM DTT, 1 mM PMSF). The cells are stirred on ice for 15 min and then centrifuged at 5000 rpms for 20 min.

Purification of GST-tagged proteins: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged protein is then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Measurement of enzyme activity: Tyrosine protein kinase assays with purified GST-Flt-3 are carried out in a final volume of 30 μL containing 200-1800 ng of enzyme protein (depending on the specific activity), 20 mM Tris-HCl, pH 7.6, 3 mM MnCl$_2$, 3 mM MgCl$_2$, 1 mM DTT, 10 μM Na$_3$VO$_4$, 3 μg/mL poly(Glu, Tyr) 4:1, 1% DMSO, 8.0 μM ATP and 0.1 μCi [γ$^{33}$P] ATP. The activity is assayed in the presence or absence of inhibitors, by measuring the incorporation of $^{33}$P from [γ$^{33}$P] ATP into the poly(Glu, Tyr) substrate. The assay (30 μL) is carried out in 96-well plates at ambient temperature for 20 min and terminated by the addition of 20 μL of 125 mM EDTA. Subsequently, 40 μL of the reaction mixture is transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum is connected and each well rinsed with 200 μL 0.5% H$_3$PO$_4$. Membranes are removed and washed 4× on a shaker with 1.0% H$_3$PO$_4$, once with ethanol. Membranes are counted after drying at ambient temperature, mounting in Packard TopCount 96-well frame, and addition of 10 μL/well of Microscint™ (Packard). IC$_{50}$ values are calculated by linear regression analysis of the percentage inhibition of each compound in duplicate, at four concentrations (usually 0.01, 0.1, 1 and 10 μM). One unit of protein kinase activity is defined as 1 nmole of $^{33}$P transferred from [γ$^{33}$P] ATP to the substrate protein per minute per mg of protein at 37° C. The compounds of the formula I here show IC$_{50}$ values in the range between 0.005 and 1 μM, especially between 0.01 and 0.5 μM, most especially between 0.01 and 0.1 μM.

Flt-3 (FMD-like tyrosine kinase) is especially expressed in hematopoietic progenitor cells and in progenitors of the lymphoid and myeloid series. Aberrant expression of the Flt-3 gene has been documented in both adult and childhood leukemias including AML (acute myelogenous leukemia), AML with trilineage myelodysplasia (AML/TMDS), ALL (acute lymphoblastic leukemia), CML (chronic myelogenous leukemia) and myelodysplastic syndrome (MDS), which are therefore the preferred diseases to be treated with compounds of the formula I. Activating mutations in Flt-3 have been found in approximately 25 to 30% of patients with AML. Thus there is accumulating evidence for the role of Flt-3 in human leukemias and the compounds of the formula I as Flt-3 inhibitors are especially of use in the therapy of this type of diseases (see Tse et al., Leukemia 15 (7), 1001-1010 (2001); Tomoki et al., Cancer Chemother. Pharmacol. 48 (Suppl. 1), S27-S30 (2001); Birkenkamp et al., Leukemia 15 (12), 1923-1921 (2001); Kelly et al., Neoplasia 99 (1), 310-318 (2002)).

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred.

Special preference is given to a compound of formula I, wherein

Q is S and X is C, or

Q is CH and X is N;

R$_1$ is phenyl that is optionally substituted by hydroxy, lower alkoxy, pyrrolidinyl-lower alkoxy, piperidinyl-lower alkoxy, morpholinyl-lower alkoxy, N,N-di-lower alkylamino-lower alkyl, N,N-di-lower alkylamino-lower alkoxy or lower alkyl-piperazinyl; and R$_2$ is thiophenyl or phenyl that is optionally substituted by halo, hydroxy, lower alkoxy or N,N-di-lower alkylamino-lower alkoxy;

or a salt thereof.

Special preference is further given to a compound of formula I, wherein

Q is S and X is C, or

Q is CH and X is N;

R$_1$ is phenyl that is optionally substituted by one or more radicals selected from the group consisting of hydroxy, lower alkyl, halogen-lower alkyl, lower alkoxy, pyrrolidinyl-lower alkoxy wherein the pyrrolidinyl moiety is optionally substituted by lower alkyl, piperidinyl-lower alkoxy, morpholinyl-lower alkoxy, N,N-di-lower alkylamino-lower alkyl, N,N-di-lower alkylamino-lower alkoxy and lower alkyl-piperazinyl; and R$_2$ is thiophenyl or phenyl that is optionally substituted by halo, hydroxy, lower alkoxy or N,N-di-lower alkylamino-lower alkoxy;

or a salt thereof.

Very special preference is given to a compound of formula I, wherein Q is S and X is C or Q is CH and X is N and $R_1$ and $R_2$ are selected independently of one another from the different meanings given for these substituents in the Examples below, or a salt, especially a pharmaceutically acceptable salt, of such a compound.

Most special preference is further given to a compound of formula I mentioned in the Examples below, or a salt, especially a pharmaceutically acceptable salt, thereof. Very preferred is also the method of synthesis for these compounds analogously to the methods described in the Examples.

The compounds of formula I or salts thereof are prepared in accordance with processes known per se, though not previously described for the manufacture of the compounds of the formula I, especially whereby (a) in order to prepare a compound of formula I wherein Q is S and X is C, a compound of formula II

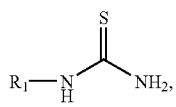

wherein $R_1$ is as defined for a compound of formula I, is reacted with a compound of the formula $R_2$—CH(Hal)-C(=O)—H, wherein Hal is halo and $R_2$ is as defined for a compound of formula I;

(b) in order to prepare a compound of formula I wherein $R_2$ is phenyl substituted by unsubstituted or substituted lower alkoxy wherein phenyl may be optionally further substituted, a compound of formula III

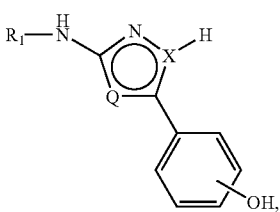

wherein $R_1$, Q and X have the meanings as defined for a compound of formula I and the phenyl ring of the compound of formula III may in addition to the hydroxy group be optionally further substituted, is reacted with halo-lower alkyl, wherein the lower alkyl moiety is optionally substituted;

(c) in order to prepare a compound of formula I wherein $R_1$ is phenyl substituted by unsubstituted or substituted lower alkoxy wherein phenyl may be optionally further substituted, a compound of formula IV

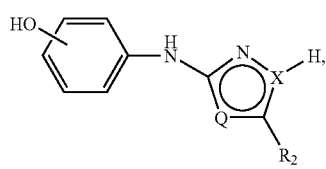

wherein $R_2$, Q and X have the meanings as defined for a compound of formula I and the phenyl ring of the compound of formula III may in addition to the hydroxy group be optionally further substituted, is reacted with halo-lower alkyl, wherein the lower alkyl moiety is optionally substituted;

(d) in order to prepare a compound of formula I wherein Q is S and X is C, a compound of formula V

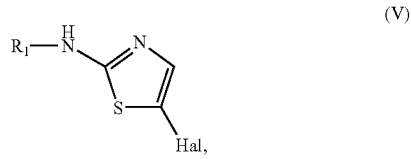

wherein Hal is halo and $R_1$ is as defined for a compound of formula I, is reacted with $R_2$—B(OH)$_2$, wherein $R_2$ is as defined for a compound of formula I; or (e) in order to prepare a compound of formula I wherein Q is CH and X is N, a compound of formula VI

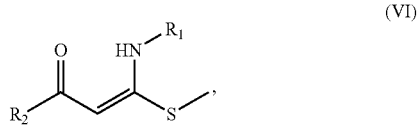

wherein $R_1$ and $R_2$ have the meanings as defined for a compound of formula I, is reacted with hydrazine;

wherein functional groups which are present in the starting compounds of processes (a) to (e) and are not intended to take part in the reaction, are present in protected form if necessary, and protecting groups that are present are cleaved, wherein said starting compounds may also exist in the form of salts provided that a salt-forming group is present and a reaction in salt form is possible;

and, if so desired, a compound of formula I thus obtained is converted into another compound of formula I, a free compound of formula I is converted into a salt, an obtained salt of a compound of formula I is converted into the free compound or another salt, and/or a mixture of isomeric compounds of formula I is separated into the individual isomers.

Description of the Process Variants

Regarding Process (a):

The reaction between a compound of formula II and a compound of the formula $R_2$—CH(Hal)-C(=O)—H preferably takes place in a suitable inert solvent, especially acetonitrile, at elevated temperatures, preferably above 50° C. In a compound of the formula $R_2$—CH(Hal)-C(=O)—H, Hal is preferably bromo.

Regarding Processes (b) and (c):

The reaction between a compound of formula III or IV and halo-lower alkyl, wherein the lower alkyl moiety is optionally substituted, preferably takes place in a suitable inert solvent, especially alcohols, e.g. lower alcohols, preferably 1-butanol, in the presence of a base, preferably a strong base, especially a metal alcoholate such as sodium tert-butoxide, at elevated temperatures, preferably at around 100° C.

Regarding Process (d):

The reaction between a compound of formula V and a compound of the formula $R_2$—$B(OH)_2$ preferably takes place in a suitable solvent, preferably toluene, in the presence of a base such as $Na_2CO_3$ and a catalyst such as $Pd(PPh_3)_4$, and in an inert, for example an argon, atmosphere, at elevated temperature, preferably at the reflux temperature of the solvent employed. In a compound of formula V, Hal is preferably bromo.

Regarding Process (e):

The reaction between a compound of formula VI and hydrazine preferably takes place in a suitable inert solvent, especially alcohols, e.g. lower alcohols, preferably ethanol, and in an inert, for example an argon, atmosphere, at elevated temperatures, preferably at around 80° C.

Additional Process Steps

In the additional process steps, carried out as desired, functional groups of the starting compounds which should not take part in the reaction may be present in unprotected form or may be protected for example by one or more protecting groups. The protecting groups are then wholly or partly removed according to one of the known methods.

Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

The end products of formula I may however also contain substituents that can also be used as protecting groups in starting materials for the preparation of other end products of formula I. Thus, within the scope of this text, only a readily removable group that is not a constituent of the particular desired end product of formula I is designated a "protecting group", unless the context indicates otherwise.

General Process Conditions

All process steps described here can be carried out under known reaction conditions, preferably under those specifically mentioned, in the absence of or usually in the presence of solvents or diluents, preferably those that are inert to the reagents used and able to dissolve them, in the absence or presence of catalysts, condensing agents or neutralising agents, for example ion exchangers, typically cation exchangers, for example in the $H^+$ form, depending on the type of reaction and/or reactants at reduced, normal, or elevated temperature, for example in the range from −100° C. to about 190° C., preferably from about −80° C. to about 150° C., for example at −80 to −60° C., at RT, at −20 to 40° C., at 0 to 100° C. or at the boiling point of the solvent used, under atmospheric pressure or in a closed vessel, if need be under pressure, and/or in an inert, for example an argon or nitrogen, atmosphere.

The invention relates also to those embodiments of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention under those process conditions, and further processes the said compound in situ. In the preferred embodiment, one starts from those starting materials which lead to the compounds described hereinabove as preferred.

In the preferred embodiment, a compound of formula I is prepared according to the processes and process steps defined in the Examples.

The compounds of formula I, including their salts, are also obtainable in the form of hydrates, or their crystals can include for example the solvent used for crystallisation (present as solvates).

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

The starting materials used in the above described process are known, capable of being prepared according to known processes, or commercially obtainable; in particular, they can be prepared using processes as described in the Examples.

In the preparation of starting materials, existing functional groups which do not participate in the reaction should, if necessary, be protected. Preferred protecting groups, their introduction and their removal are described above or in the Examples. In place of the respective starting materials and transients, salts thereof may also be used for the reaction, provided that salt-forming groups are present and the reaction with a salt is also possible. Where the term starting materials is used hereinbefore and hereinafter, the salts thereof are always included, insofar as reasonable and possible.

A compound of formula II can be prepared for example by reacting a compound of the formula VII

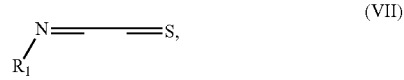

wherein $R_1$ is as defined for a compound of formula I, with ammonia, in a suitable inert solvent, especially alcohols, e.g. lower alcohols, such as methanol, and in an inert, for example an argon, atmosphere, at elevated temperature, preferably at around 60° C.

A compound of formula VII can be prepared for example by reacting a compound of the formula $R_1$—$NH_2$, wherein $R_1$ is as defined for a compound of formula I, with thiophosgene, in a suitable solvent, e.g. halogenated hydrocarbon, typically chloroform, in the presence of a suitable base, such as $NaCO_3$, preferably at room temperature.

A compound of the formula $R_2$—CH(Hal)-C(=O)—H can be prepared for example by reacting a compound of the formula $R_2$—$CH_2$—C(=O)—H, wherein $R_2$ is as defined for a compound of formula I, with $Me_3SiBr$, in a suitable solvent such as acetonitrile, in the presence of dimethyl sulfoxide and in an inert, for example an argon, atmosphere, preferably at 0° C. or below.

A compound of formula V can be prepared for example by reacting a compound of the formula VIII

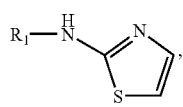

(VIII)

wherein $R_1$ is as defined for a compound of formula I, with Hal-Hal, wherein Hal is halo, preferably bromo, in a suitable inert solvent, such as N,N-dimethyl-formamide, and in an inert, for example an argon, atmosphere, preferably at room temperature.

A compound of formula VIII can be prepared for example by reacting a compound of the formula II, wherein $R_1$ is as defined for a compound of formula I, with chloroacetaldehyde, in a suitable inert solvent, especially alcohols, e.g. lower alcohols, such as ethanol, at elevated temperatures, preferably at the reflux temperature of the solvent employed.

A compound of formula VI can be prepared for example by (i) reacting a compound of the formula $R_2-C(=O)-CH_3$ with NaH in a suitable inert solvent, such as N,N-dimethyl-formamide, preferably at around 0° C., (ii) adding to the reaction mixture a compound of formula VIII, wherein $R_1$ is as defined for a compound of formula I, the reaction preferably taking place at room temperature, and (iii) reacting the reaction mixtures with $CH_3I$, preferably at room temperature.

The remaining starting materials are known, capable of being prepared according to known processes, or commercially available; or in particular, they can be prepared using processes as described in the Examples.

Pharmaceutical Compositions, Methods, and Uses

The present invention relates also to pharmaceutical compositions that comprise a compound of formula I, or a pharmaceutically acceptable salt thereof, as active ingredient and that can be used especially in the treatment of the diseases mentioned above. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions contain the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

The invention relates also to compounds of formula I, or a pharmaceutically acceptable salt thereof, as such or in the form of a pharmaceutical composition, for use in a method for the prophylactic or especially therapeutic treatment of the human or animal body, to a process for the preparation thereof (especially in the form of compositions for the treatment of tumours) and to a method of treating proliferative diseases, primarily tumour diseases, especially those mentioned above.

The invention relates also to processes and to the use of compounds of formula I, or a pharmaceutically acceptable salt thereof, for the preparation of pharmaceutical compositions which comprise compounds of formula I, or a pharmaceutically acceptable salt thereof, as active component (active ingredient).

If desired, the said pharmaceutical compositions may also contain further active components, for example cytostatics, and/or may be used in combination with known therapeutic processes, for example the administration of hormones or radiation.

Preference is given for a pharmaceutical composition which is suitable for administration to a warm-blooded animal, especially humans or commercially useful mammals suffering from a disease which responds to an inhibition of a protein tyrosine kinase, especially to an inhibition of Flt-3, especially a neoplastic disease, comprising an effective quantity of a compound of formula I for the inhibition of a protein tyrosine kinase, especially for the inhibition of Flt-3, or a pharmaceutically acceptable salt thereof, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against said diseases a compound of formula I, or a pharmaceutically acceptable salt thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories or capsules. Examples are capsules containing from about 0.05 g to about 1.0 g of active substance.

The pharmaceutical compositions of the present invention are prepared in a manner known per se, for example by means of conventional mixing, granulating, coating, dissolving or lyophilising processes.

The invention relates likewise to a process or a method for the treatment of one of the pathological conditions mentioned hereinabove, especially a disease which responds to an inhibition of a protein tyrosine kinase, especially to an inhibition of Flt-3, especially a corresponding neoplastic disease. The compounds of formula I, or pharmaceutically acceptable salts thereof, can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a bodyweight of about 70 kg the daily dose administered is from approximately 0.05 g to approximately 2 g, preferably from approximately 0.1 g to approximately 1 g, of a compound of the present invention.

The present invention relates especially also to the use of a compound of formula I, or a pharmaceutically acceptable salt thereof, especially a compound of formula I which is said to be preferred, or a pharmaceutically acceptable salt thereof, as such or in the form of a pharmaceutical composition with at least one pharmaceutically acceptable carrier, for the therapeutic and also prophylactic management of one or more of the diseases mentioned hereinabove, preferably a disease which responds to an inhibition of a protein tyrosine kinase, especially to an inhibition of Flt-3, especially a neoplastic disease, in particular if the said disease responds to an inhibition of a protein tyrosine kinase, especially to an inhibition of Flt-3.

The present invention relates especially also to the use of a compound of formula I, or a pharmaceutically acceptable salt thereof, especially a compound of formula I which is said to be preferred, or a pharmaceutically acceptable salt thereof, for the preparation of a pharmaceutical composition for the therapeutic and also prophylactic management of one or more of the diseases mentioned hereinabove, especially a neoplastic disease, in particular if the disease responds to an inhibition of a protein tyrosine kinase, especially to an inhibition of Flt-3.

A compound of the formula I may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, steroids, antiproliferative antibodies, 17-(allylamino)-17-demethoxygeldanamycin (17-AAG) and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is not limited to topotecan, irinotecan, 9-nitrocamptothecin and the macromolecular camptothecin conjugate PNU-166148 (compound A1 in WO 99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., in the form as it is marketed, e.g. under the trademark ZAVEDOS™; Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes Suberoylanilide hydroxamic acid (SAHA).

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCl-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, the Platelet-derived Growth Factor (PDGF), Bcr-Abl, c-Kit, Flt-3, the Insulin-like Growth Factor I Receptor (IGF-IR) and the Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88, 1997, 277-285;

compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO 97/07131 and WO 97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO 97/32879 and WO 97/49706;

compounds which decreases the activity of the protein kinase C are especially those staurosporine derivatives disclosed in EP 0 296 110 (pharmaceutical preparation described in WO 00/48571) which compounds are protein kinase C inhibitors; compounds which decrease the activity of IGF-IR are especially those compounds disclosed in WO 02/92599;

further specific compounds that decrease protein kinase activity and which may also be used in combination with the compounds of the present invention are Imatinib (Gleevec®/Glivec®), PKC412, Iressa™ (ZD1839), {6-[4-(4-ethyl-piperazin-1-ylmethyl)-phenyl]-7H-pyrrolo[2,3-d]pyrimidin-4-yl}-((R)-1-phenyl-ethyl)-amine (AEE788) and pharmaceutically acceptable salts thereof (see also WO 03/13541), 1-(4-chloro-anilino)-4-(4-pyridyl-methyl)-phthalazine (PTK787) and pharmaceutically acceptable salts thereof (see also WO 98/35958), ZD6474, GW2016, CHIR-200131, CEP-7055/CEP-5214, CP-547632, KRN-633 and SU5416;

anti-angiogenic compounds having another mechanism of action than decreasing the protein kinase activity include, but are not limited to e.g. thalidomide (THALOMID), celecoxib (Celebrex) and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, e.g. as disclosed in U.S. Pat. No. 5,843,901.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having antiproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "steroids" includes hydrocortisone, dexamethasone (Decadron®), methylprednisolone and prednisolone.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyltransferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

EXAMPLES

The following Examples serve to illustrate the invention without limiting its scope.

Temperatures are measured in degrees Celsius. Unless otherwise indicated, the reactions take place at room temperature.

The $R_f$ values which indicate the ratio of the distance moved by each substance to the distance moved by the eluent front are determined on silica gel thin-layer plates (Merck, Darmstadt, Germany) by thin-layer chromatography using the respective named solvent systems.

Analytical HPLC Conditions:

System 1

Linear gradient 2-100% $CH_3CN$ (0.1% trifluoroacetic acid (TFA)) and $H_2O$ (0.1% TFA) in 10 min+2 min 100% $CH_3CN$ (0.1% TFA); detection at 215 nm, flow rate 0.7 mL/min at 30° C.

Column: Nucleosil 120-3 C18 (125×3.0 mm)

System 2

Linear gradient 20-100% $CH_3CN$ in 5 min+1.5 min 100% $CH_3CN$ (0.1% TFA); detection at 215 nm; flow rate 1 mL/min at 30° C. Column: Nucleosil 100-3 C18 (70×4.0 mm)

System 3

Linear gradient 2-100% $CH_3CN$ in 10 min+3 min 100% $CH_3CN$ (0.1% TFA); detection at 215 nm, flow rate 2 mL/min at 30° C. Column: Nucleosil 100-3 C18 (250×4.6 mm)

Abbreviations:

DIEA N-ethyldiisopropylamine

DMF N,N-dimethyl-formamide

DMSO dimethyl sulfoxide

Et ethyl

EtOH ethanol equiv equivalent(s)

ES-MS electron spray-mass spectroscopy h hour(s)

HPLC high pressure liquid chromatography

Me methyl min minute(s)

MPLC medium pressure liquid chromatography

RT room temperature

TFA trifluoroacetic acid $t_R$ retention times

Thiazoles

Example 1

(5-Phenyl-thiazol-2-yl)-[4-(2-pyrrolidin-1-yl-ethoxy)-phenyl]-amine

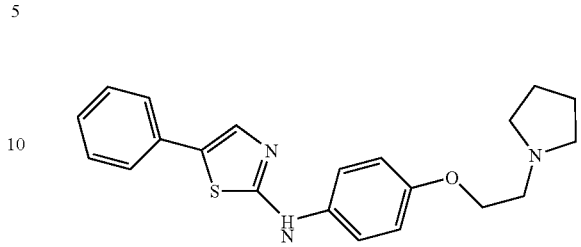

$Me_3SiBr$ (0.052 mL, 0.384 mmol, 1.1 equiv) and DMSO (0.027 mL, 0.384 mmol, 1.1 equiv) are added sequentially and dropwise to a cold (0° C.) solution of phenylacetaldehyde (42 mg, 0.349 mmol) in $CH_3CN$ (0.66 mL), under an argon atmosphere. The resulting mixture is stirred at 0° C. for 50 min, allowed to warm to RT and to stir for 10 min. $CH_3CN$ (0.97 mL) is added to the reaction mixture, followed by addition of [4-(2-pyrrolidin-1-yl-ethoxy)-phenyl]-thiourea (93 mg, 0.349 mmol). The reaction mixture is heated to reflux for 80 min, allowed to cool to RT and concentrated in vacuo. Purification of the crude product by silica gel (20 g) column chromatography ($CH_2Cl_2$/MeOH, 90/10) affords the title compound: ES-MS: 366.0 $[M+H]^+$; single peak at $t_R$=6.33 min (System 1); $R_f$=0.11 ($CH_2Cl_2$/MeOH, 80/20).

[4-(2-Pyrrolidin-1-yl-ethoxy)-phenyl]-urea

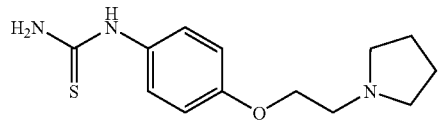

A mixture of 1-[2-(4-isothiocyanato-phenoxy)-ethyl]-pyrrolidine (0.355 g, 1.43 mmol), MeOH (2.75 mL) and a 2M solution of $NH_3$ in MeOH (2.75 mL, 5.49 mmol, 3.84 equiv) is heated in a sealed tube at 60° C. for 1 h, under an argon atmosphere. The reaction mixture is allowed to cool to RT and concentrated in vacuo to afford the title compound as a dark brown solid: ES-MS: 266.0 $[M+H]^+$; single peak at $t_R$=3.99 min (System 1).

1-[2-(4-Isothiocyanato-phenoxy)-ethyl]-pyrrolidine

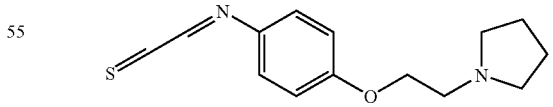

A solution of thiophosgene (150 μL, 1.76 mmol, 1.2 equiv) in $CHCl_3$ (2.7 mL) is added to a vigorously stirred mixture of 4-(2-pyrrolidin-1-yl-ethoxy)-phenylamine (0.303 g, 1.47 mmol) in $CHCl_3$ (7.5 mL) and a saturated aqueous solution of $NaHCO_3$ (7.5 mL). The resulting dark mixture is stirred at RT for 1 h. The layers are separated and the aqueous phase is extracted with $CHCl_3$. The organic phase is washed with brine, dried ($Na_2SO_4$), filtered and concentrated in vacuo to afford the title compound as a dark oil: ES-MS: 249.0 [M+H]$^+$; single peak at $t_R$=6.90 min (System 1).

4-(2-Pyrrolidin-1-yl-ethoxy)-phenylamine

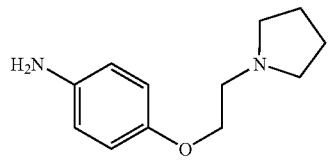

A mixture of 4-aminophenol (4.0 g, 37.4 mmol), 1-(2-chloroethyl)-pyrrolidine hydrochloride (7.6 g, 44.9 mmol, 1.2 equiv), NaOH (3.7 g, 93.5 mmol, 2.5 equiv) in DMF (64 mL) is stirred for 2 h at 75° C., under an argon atmosphere. The mixture is allowed to cool to RT and then filtered through a glass sintered funnel. The filtrate is diluted with CH$_2$Cl$_2$ (200 mL), washed with brine (2×50 mL), dried (Na$_2$SO$_4$), filtered and concentrated. The residue is purified by silica gel (260 g) column chromatography (CH$_2$Cl$_2$/MeOH, 70/30→50/50) to afford the title compound as a dark brown oil: ES-MS: 207.1 [M+H]$^+$; $R_f$=0.18 (CH$_2$Cl$_2$/MeOH, 50/50).

Example 2

(3-Dimethylaminomethyl-phenyl)-(5-phenyl-thiazol-2-yl)-amine

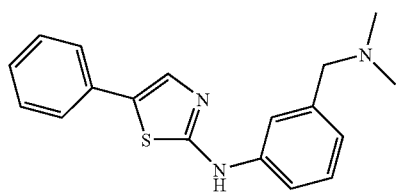

The title compound is prepared as described in Example 1 for (5-phenyl-thiazol-2-yl)-[4-(2-pyrrolidin-1-yl-ethoxy)phenyl]-amine but using (3-dimethylaminomethyl-phenyl)-thiourea. Title compound: ES-MS: 310.1 [M+H]$^+$; single peak at $t_R$=6.65 min (System 1); $R_f$=0.63 (CH$_2$Cl$_2$/MeOH, 80/20).

(3-Dimethylaminomethyl-phenyl)-thiourea

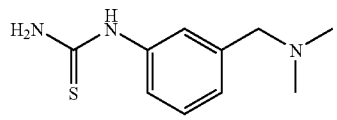

The title compound is prepared as described in Example 1 for [4-(2-pyrrolidin-1-yl-ethoxy)-phenyl]-urea but using (3-isothiocyanato-benzyl)-dimethyl-amine. Title compound: ES-MS: 210.0 [M+H]$^+$; single peak at $t_R$=3.38 min (System 1); $R_f$=0.63 (CH$_2$Cl$_2$/MeOH, 80/20). (3-Isothiocyanato-benzyl)-dimethyl-amine is prepared as described in Example 1 for 1-[2-(4-isothiocyanato-phenoxy)ethyl]-pyrrolidine but using 3-dimethylaminomethyl-phenylamine. (3-Isothiocyanato-benzyl)dimethyl-amine is obtained and used as an impure crude material.

Example 3

[5-(4-Methoxy-phenyl)-thiazol-2-yl]-[4-(2-pyrrolidin-1-yl-ethoxy)-phenyl]-amine

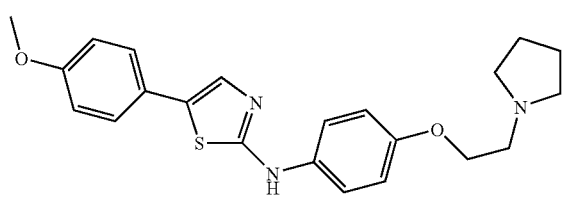

The title compound is prepared as described in Example 1 for (5-phenyl-thiazol-2-yl)-[4-(2-pyrrolidin-1-yl-ethoxy)phenyl]-amine but using (4-methoxy-phenyl)-acetaldehyde. Title compound: ES-MS: 396.0 [M+H]$^+$; single peak at $t_R$=6.36 min (System 1); $R_4$=0.28 (CH$_2$Cl$_2$/MeOH, 80/20).

(4-Methoxy-phenyl)-acetaldehyde

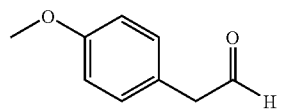

Dess-Martin periodinane (3.2 g, 7.29 mmol, 1.1 equiv) is added in one portion to a mixture of 4-methoxyphenethyl alcohol (1.0 g, 6.63 mmol) and NaHCO$_3$ (1.1 g, 13.2 mmol, 2.0 equiv) in CH$_2$Cl$_2$, under an argon atmosphere. The resulting mixture is stirred for 1 h at RT and directly loaded on a silica gel (60 g) column. Flash chromatography purification (CH$_2$Cl$_2$/Et$_2$O, 95/5), affords the title compound as a colorless oil: ES-MS: 148.9 [M–H]$^-$; single peak at $t_R$=6.12 min (System 1); $R_f$=0.74 (CH$_2$Cl$_2$/Et$_2$O, 95/5).

Example 4

(4-Methoxy-phenyl)-[5-(4-methoxy-phenyl)-thiazol-2-yl]-amine

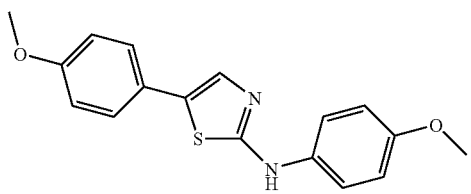

The title compound is prepared as described in Example 3 for [5-(4-methoxy-phenyl)-thiazol-2-yl]-[4-(2-pyrrolidin-1-yl-ethoxy)-phenyl]-amine but using (4-methoxy-phenyl)-thiourea. After addition of the thiourea and subsequent heating to reflux, the reaction mixture is allowed to cool to RT. DIEA (2.0 equiv) is added and the resulting mixture is heated to reflux for 70 min. Purification of the crude product by silica gel (40 g) column chromatography (CH$_2$Cl$_2$/Et$_2$O, 95/5) affords the title compound as a beige solid: ES-MS: 312.9 [M+H]$^+$; single peak at t$_R$=7.66 min (System 1); R$_f$=0.11 (CH$_2$Cl$_2$/MeOH, 95/5).

Example 5

[5-(4-Methoxy-phenyl)-thiazol-2-yl]-[4-(4-methyl-piperazin-1-yl)-phenyl]-amine

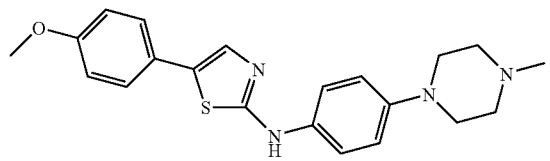

The title compound is prepared as described in Example 3 for [5-(4-methoxy-phenyl)-thiazol-2-yl]-[4-(2-pyrrolidin-1-yl-ethoxy)-phenyl]-amine but using [4-(4-methyl-piperazin-1-yl)-phenyl]-thiourea. Purification of the crude product by silica gel (20 g) column chromatography (CH$_2$Cl$_2$/MeOH, 90/10) and subsequent washing of the purified product with MeOH affords the title compound as a light beige solid: ES-MS: 381.0 [M+H]$^+$; single peak at t$_R$=6.13 min (System 1); R$_f$=0.53 (CH$_2$Cl$_2$/MeOH, 80/20).

[4-(4-Methyl-piperazin-1-yl)-phenyl]-thiourea

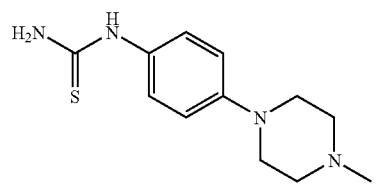

The title compound is prepared as described in Example 1 for [4-(2-pyrrolidin-1-yl-ethoxy)-phenyl]-urea but using 1-(4-isothiocyanato-phenyl)-4-methyl-piperazine and stirring the reaction mixture at RT for 17 h. Title compound: ES-MS: 251.0 [M+H]$^+$; major peak at t$_R$=3.56 min (System 1); R$_f$=0.27 (CH$_2$Cl$_2$/MeOH, 80/20).

1-(4-Isothiocyanato-phenyl)-4-methyl-piperazine

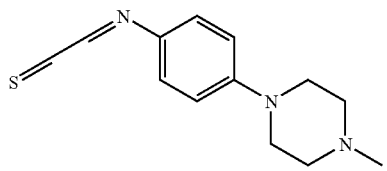

The title compound is prepared as described in Example 1 for 1-[2-(4-isothiocyanato-phenoxy)-ethyl]-pyrrolidine but using 4-(4-methyl-piperazin-1-yl)-phenylamine. Title compound: ES-MS: 234.0 [M+H]$^+$; single peak at t$_R$=6.60 min (System 1).

4-(4-Methyl-piperazin-1-yl)-phenylamine can be prepared according to literature procedures: Loewe, Heinz; Mieth, H.; Urbanietz, Josef. 4-Aminoquinoline. Arzneimittel-Forschung (1966), 16(10), 1306-10.

Example 6

[4-(2-Dimethylamino-ethoxy)-phenyl]-[5-(4-methoxy-phenyl)thiazol-2-yl]-amine

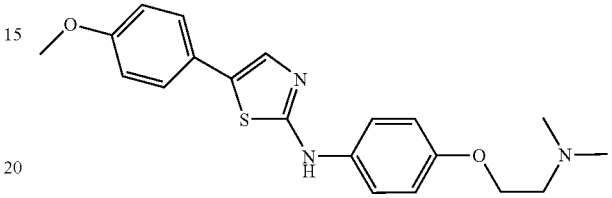

The title compound is prepared as described in Example 3 for [5-(4-methoxy-phenyl)-thiazol-2-yl]-[4-(2-pyrrolidin-1-yl-ethoxy)-phenyl]-amine but using [4-(2-dimethylamino-ethoxy)-phenyl]-thiourea. Title compound: ES-MS: 370.0 [M+H]$^+$; single peak at t$_R$=6.13 min (System 1); R$_f$=0.13 (CH$_2$Cl$_2$/MeOH, 80/20).

[4-(2-Dimethylamino-ethoxy)-phenyl]-thiourea

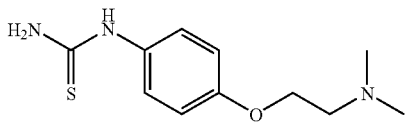

The title compound is prepared as described in Example 1 for [4-(2-pyrrolidin-1-yl-ethoxy)-phenyl]-urea but using [2-(4-isothiocyanato-phenoxy)-ethyl]-dimethyl-amine. The title compound: ES-MS: 240.0 [M+H]$^+$; single peak at t$_R$=3.52 min (System 1).

[2-(4-Isothiocyanato-phenoxy)-ethyl]-dimethyl-amine

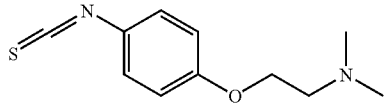

The title compound is prepared as described in Example 1 for 1-[2-(4-isothiocyanato-phenoxy)-ethyl]-pyrrolidine but using 4-(2-dimethylamino-ethoxy)-phenylamine. Title compound: ES-MS: 223.0 [M+H]$^+$; single peak at t$_R$=6.52 min (System 1).

4-(2-Dimethylamino-ethoxy)-phenylamine

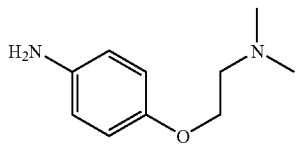

The title compound is prepared as described in Example 1 for 4-(2-pyrrolidin-1-yl-ethoxy)-phenylamine but using 1-chloro-2-dimethylaminoethane hydrochloride. Title compound: ES-MS: 181.2 [M+H]$^+$; R$_f$=0.18 (CH$_2$Cl$_2$/MeOH, 70/30).

Example 7

4-{2-[4-(2-Pyrrolidin-1-yl-ethoxy)-phenylamino]-thiazol-5-yl}-phenol

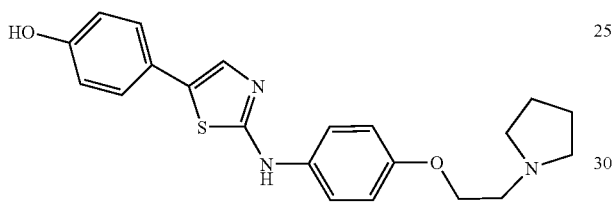

A 1 N solution of BBr$_3$ in CH$_2$Cl$_2$ (0.4 mL, 0.404 mmol, 8.0 equiv) is added dropwise to a cold (−10° C.) solution of [5-(4-methoxy-phenyl)thiazol-2-yl]-[4-(2-pyrrolidin-1-yl-ethoxy)-phenyl]-amine (Example 3) (20 mg, 0.0506 mmol) in CH$_2$Cl$_2$ (0.4 mL), under an argon atmosphere. The reaction mixture is allowed to warm to RT and to stir for 1.5 h. The mixture is then cooled to 0° C. and quenched with MeOH. The resulting red solution is concentrated in vacuo. Purification of the crude material by silica gel (9 g) column chromatography (CH$_2$Cl$_2$/MeOH, 90/10) affords the title compound as a beige solid: ES-MS: 382.0 [M+H]$^+$; single peak at t$_R$=5.47 min (System 1); R$_f$=0.28 (CH$_2$Cl$_2$/MeOH, 80/20).

Example 8

{5-[4-(3-Dimethylamino-propoxy)-phenyl]-thiazol-2-yl}-phenyl-amine

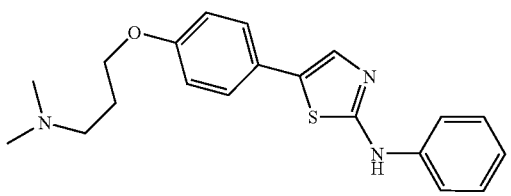

A mixture of 4-(2-phenylamino-thiazol-5-yl)-phenol (35 mg, 0.130 mmol), 1-chloro-3-dimethylaminopropane hydrochloride (27 mg, 0.170 mmol, 1.3 equiv), and sodium tert-butoxide (29.6 mg, 0.299 mmol, 2.3 equiv) in 1-butanol (0.2 mL) is heated to 100° C. (using a preheated oil bath) for 3.5 h. The reaction mixture is allowed to cool to RT and concentrated in vacuo. Purification of the crude material by silica gel (10 g) column chromatography (CH$_2$Cl$_2$/MeOH, 90/10→80/20) affords the title compound as a reddish solid: ES-MS: 354.0 [M+H]$^+$; single peak at t$_R$=6.27 min (System 1); R$_f$=0.09 (CH$_2$Cl$_2$/MeOH, 90/10).

4-(2-Phenylamino-thiazol-5-yl)-phenol

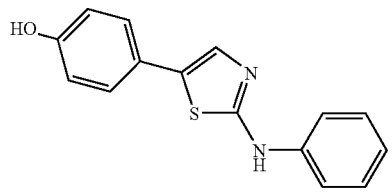

The title compound is prepared as described in Example 7 for 4-{2-[4-(2-pyrrolidin-1-yl-ethoxy)-phenylamino]-thiazol-5-yl}-phenol but starting from [5-(4-methoxy-phenyl)-thiazol-2-yl]-phenyl-amine and using 2 equivalents of BBr$_3$. Title compound: ES-MS: 269.0 [M+H]$^+$; single peak at t$_R$=6.65 min (System 1); R$_f$=0.05 (CH$_2$Cl$_2$/MeOH, 98/2).

[5-(4-Methoxy-phenyl)-thiazol-2-yl]-phenyl-amine

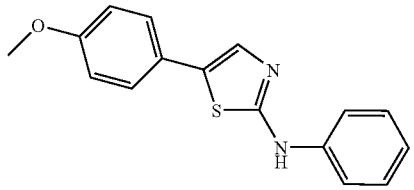

The title compound is prepared as described in Example 4 for (4-methoxy-phenyl)-[5-(4-methoxy-phenyl)thiazol-2-yl]-amine but using phenylthiourea. Title compound: ES-MS: 283.0 [M+H]$^+$; single peak at t$_R$=7.89 min (System 1); R$_f$=0.50 (CH$_2$Cl$_2$/MeOH, 98/2).

Example 9

4-[5-(3-Methoxy-phenyl)-thiazol-2-ylamino]-phenol

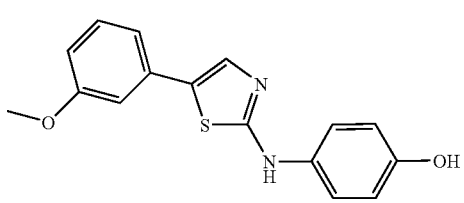

The title compound is prepared as described in Example 4 for (4-methoxy-phenyl)-[5-(4-methoxy-phenyl)-thiazol-2-yl]-amine but using (4-hydroxy-phenyl)-thiourea and 3-methoxy-phenyl)-acetaldehyde. Title compound: ES-MS:

312.9 [M−H]⁻; single peak at $t_R$=6.81 min (System 1); $R_f$=0.28 (CH$_2$Cl$_2$/MeOH, 95/5).

3-Methoxy-phenyl)-acetaldehyde

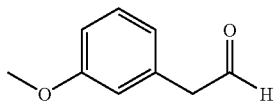

The title compound is prepared as described in Example 3 for (4-methoxy-phenyl)-acetaldehyde. Title compound: ES-MS: 148.9 [M−H]⁻; single peak at $t_R$=6.11 min (System 1); $R_f$=0.62 (CH$_2$Cl$_2$/Et$_2$O, 95/5).

Example 10

4-[5-(3-Methoxy-phenyl)-thiazol-2-yl]-[4-(2-pyrrolidin-1-yl-ethoxy)-phenyl]amine

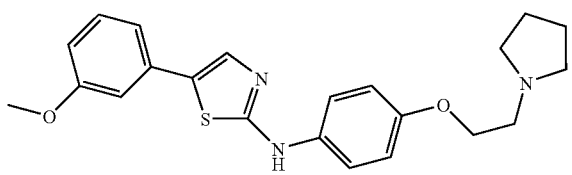

The title compound is prepared as described in Example 8 for {5-[4-(3-dimethylamino-propoxy)-phenyl]-thiazol-2-yl}-phenyl-amine but starting from 4-[5-(3-methoxy-phenyl)-thiazol-2-ylamino]-phenol (Example 9) and using 1-(2-chloroethyl)-pyrrolidine hydrochloride. After a 2 h stirring at 100° C. and usual work-up, purification of the crude product by silica gel (3 g) column chromatography (CH$_2$Cl$_2$/MeOH, 90/10→80/20), affords the title compound as a pink solid: ES-MS: 396.0 [M+H]⁺; single peak at $t_R$=6.47 min (System 1); $R_f$=0.56 (CH$_2$Cl$_2$/MeOH, 80/20).

Example 11

(4-Methoxy-phenyl)-(5-thiophen-3-yl-thiazol-2-yl)-amine

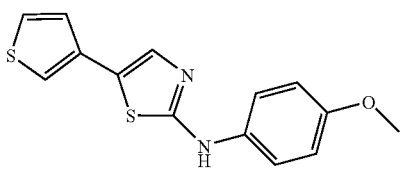

A mixture of (5-bromo-thiazol-2-yl)-(4-methoxy-phenyl)-amine (203 mg, 0.710 mmol), 3-thiophene-boronic acid (268 mg, 2.10 mmol, 6.0 equiv), Pd(PPh$_3$)$_4$ (12 mg, 0.0105 mmol, 0.03 equiv), Na$_2$CO$_3$ (326 mg, 3.08 mmol, 8.8 equiv), and water (305 μL, 16.7 mmol, 24 equiv) in toluene (10 mL) is heated in a sealed tube to 120° C. for 1 h, under an argon atmosphere. The resulting suspension is allowed to cool to RT and filtered through a pad of celite, washing the filter cake with CH$_2$Cl$_2$ and water. The layers are separated. The organic phase is dried (Na$_2$SO$_4$), filtered and concentrated. Purification by MPLC (CH$_3$CN/H$_2$O/TFA) affords the title compound as a light beige solid: ES-MS: 289.0 [M+H]⁺; single peak at $t_R$=7.43 min (System 1); $R_f$=0.56 (CH$_2$Cl$_2$/MeOH, 80/20).

(5-Bromo-thiazol-2-yl)-(4-methoxy-phenyl)-amine

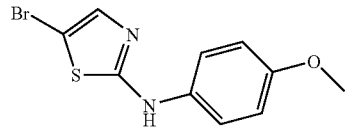

A 1 M solution of Br$_2$ in DMF (12.9 mL, 13.2 mmol) is added dropwise to a solution of (4-methoxy-phenyl)-thiazol-2-yl-amine (2.72 g, 13.2 mmol) in DMF (40 mL), under an argon atmosphere. During the addition, the internal temperature of the reaction mixture is kept below 26° C. The mixture is stirred for 20 min at 25° C. and concentrated in vacuo. Purification of the crude product by silica gel (250 g) column chromatography (CH$_2$Cl$_2$/MeOH, 99/1) affords the title compound: ES-MS: 287.0 [M+H]⁺; single peak at $t_R$=7.99 min (System 1); $R_f$=0.47 (CH$_2$Cl$_2$/MeOH, 98/2).

(4-Methoxy-phenyl)thiazol-2-yl-amine

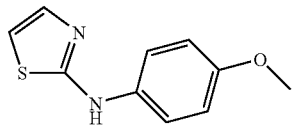

A mixture of (4-methoxy-phenyl)-thiourea (3.0 g, 16.5 mmol) and a 45% aqueous solution of chloroacetaldehyde (12 mL, 82.4 mmol, 5.0 equiv) in EtOH (23 mL) is heated to reflux for 1 h. The resulting dark orange solution is allowed to cool to RT and concentrated in vacuo. NaHCO$_3$ is then added to the oily residue until CO$_2$ evolution subsides and a beige precipitate forms. The product is collected by vacuum filtration, washed thoroughly with water (600 mL), and dried in vacuo. Title compound: ES-MS: 207.0 [M+H]⁺; single peak at $t_R$=5.32 min (System 1); $R_f$=0.17 (CH$_2$Cl$_2$/MeOH, 95/5).

Example 12

4-(5-Thiophen-3-yl-thiazol-2-yl-amino)-phenol

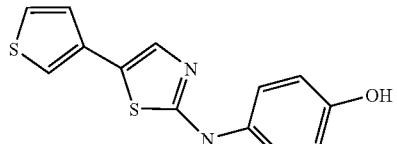

The title compound can be prepared according to two alternative protocols.

Procedure A

The title compound is prepared as described in Example 7 for 4-{2-[4-(2-pyrrolidin-1-yl-ethoxy)-phenylamino]-thiazol-5-yl}-phenol but starting from (4-methoxy-phenyl)-(5-thiophen-3-yl-thiazol-2-yl)-amine (Example 11) and using 4 equivalents of BBr$_3$. Title compound: ES-MS: 275.0 [M+H]$^+$; single peak at t$_R$=6.44 min (System 1); R$_f$=0.15 (CH$_2$Cl$_2$/MeOH, 90/10).

Procedure B

Me$_3$SiBr (1.6 mL, 12.2 mmol, 1.1 equiv) and DMSO (0.87 mL, 12.2 mmol, 1.1 equiv) are added sequentially and dropwise to a cold (−35° C.) solution of 3-thiophenylacetaldehyde (1.4 g, 11.1 mmol) in CH$_3$CN (23 mL), under an argon atmosphere. The resulting mixture is allowed to stir for 10 min. The mixture is allowed to warm to 0° C., to stir for 50 min, then to warm to room temperature and to stir for 10 min. CH$_3$CN (42 mL) is added to the reaction mixture, followed by addition of (4-hydroxyphenyl)-2-thiourea (1.86 g, 11.1 mmol). The reaction mixture is heated to 50° C. for 10 min, then stirred for 15 min at 70° C., and for 1 h at reflux. DIEA (3.8 mL, 22.2 mmol, 2.2 equiv) is then added and the resulting mixture is heated at reflux for 1 h. The reaction mixture is allowed to cool to RT and concentrated in vacuo. The crude product is purified by silica gel column chromatography (CH$_2$Cl$_2$, 100% then CH$_2$Cl$_2$/MeOH, 90/10) to afford the title compound.

3-Thiophenylacetaldehyde

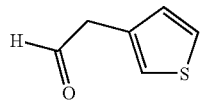

Dess-Martin Periodinane (14 g, 33 mmol) is added to a mixture of 2-(3-thienyl)-ethanol (4.0 mL, 36 mmoml, 1.10 equiv) and NaHCO$_3$ (2.8 g, 33 mmol) in CH$_2$Cl$_2$ (132 mL), under an argon atmosphere. The reaction mixture is allowed to stir at RT for 1 h. The mixture is then filtered and the filtrate directly loaded on a chromatography column. Purification by silica gel column chromatography (CH$_2$Cl$_2$/Et$_2$O, 95/5) affords the title compound as a light yellow oil. Title compound: single peak at t$_R$=2.67 min (System 2); R$_f$=0.53 (CH$_2$Cl$_2$/Et$_2$O, 95/5).

Example 13

[4-(2-Dimethylamino-ethoxy)-phenyl]-(5-thiophen-3-yl-thiazol-2-yl)-amine

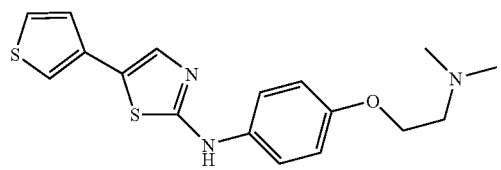

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-yl-amino)-phenol (Example 12) and using 1-chloro-2-dimethylaminoethane hydrochloride. Title compound: ES-MS: 346.0 [M+H]$^+$; single peak at t$_R$=5.89 min (System 1); R$_f$=0.34 (CH$_2$Cl$_2$/MeOH, 90/10).

Example 14

[4-(3-Dimethylamino-propoxy)-phenyl]-(5-thiophen-3-yl-thiazol-2-yl)-amine

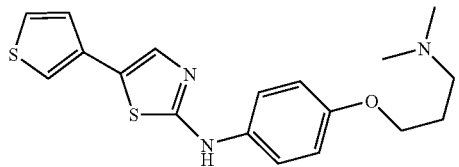

The title compound is prepared as described in Example 8 for {5-[4-(3-dimethylamino-propoxy)-phenyl]-thiazol-2-yl}phenyl-amine but starting from 4-(5-thiophen-3-yl-thiazol-2-yl-amino)-phenol (Example 12). Title compound: ES-MS: 360.0 [M+H]$^+$; single peak at t$_R$=6.16 min (System 1); R$_f$=0.12 (CH$_2$Cl$_2$/MeOH, 85/15).

Example 15

[4-(2-Pyrrolidin-1-yl-ethoxy)-phenyl]-(5-thiophen-3-yl-thiazol-2-yl)-amine

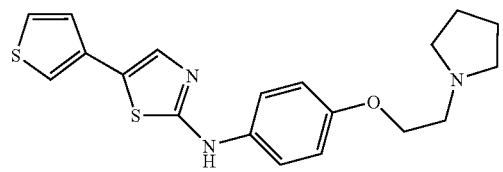

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-yl-amino)-phenol (Example 12) and using 1-(2-chloroethyl)-pyrrolidine hydrochloride. Title compound: ES-MS: 372.0 [M+H]$^+$; single peak at t$_R$=6.07 min (System 1); R$_f$=0.30 (CH$_2$Cl$_2$/MeOH, 80/20).

Example 16

[4-(2-Piperidin-1-yl-ethoxy)-phenyl]-(5-thiophen-3-yl-thiazol-2-yl)-amine

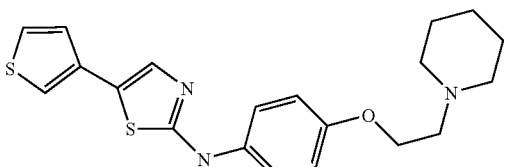

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-yl-amino)-phenol (Example 12) and using 1-(2-chloroethyl)-piperidine hydrochloride. Title compound: ES-MS: 386.0 [M+H]$^+$; single peak at t$_R$=6.26 min (System 1); R$_f$=0.36 (CH$_2$Cl$_2$/MeOH, 80/20).

Example 17

[4-(2-Diisopropylamino-ethoxy)-phenyl]-(5-thiophen-3-yl-thiazol-2-yl)-amine

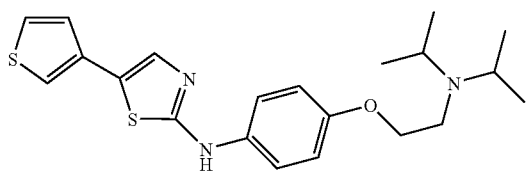

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-yl-amino)-phenol (Example 12) and using (2-chloroethyl)-diisopropyl-amine hydrochloride. Title compound: ES-MS: 402.0 [M+H]$^+$; single peak at $t_R$=6.53 min (System 1); $R_f$=0.50 (CH$_2$Cl$_2$/MeOH, 80/20).

Example 18

[4-(2-Morpholin-4-yl-ethoxy)-phenyl]-(5-thiophen-3-yl-thiazol-2-yl)-amine

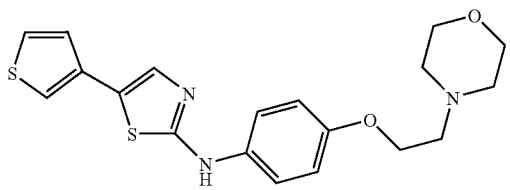

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-yl-amino)-phenol (Example 12) and using (2-chloroethyl)-morpholine hydrochloride. MPLC (CH$_3$CN/H$_2$O/TFA) purification affords the title compound: ES-MS: 388.0 [M+H]$^+$; single peak at $t_R$=2.80 min (System 2).

Example 19

(3-Dimethylaminomethyl-phenyl)-(5-thiophen-3-yl-thiazol-2-yl)-amine

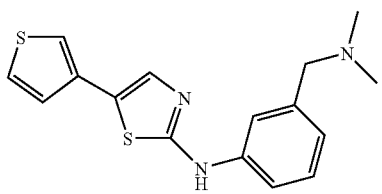

Me$_3$SiBr (0.23 mL, 1.75 mmol, 1.1 equiv) and DMSO (0.12 mL, 1.75 mmol, 1.1 equiv) are added sequentially and dropwise to a cold (−35° C.) solution of 3-thiophenylacetaldehyde (200 mg, 1.59 mmol) in CH$_3$CN (3.0 mL), under an argon atmosphere. The resulting mixture is allowed to warm to 0° C., to stir for 50 min, then to warm to room temperature and to stir for 10 min. CH$_3$CN (5.0 mL) is added to the reaction mixture, followed by addition of (3-dimethylaminomethyl-phenyl)-thiourea (Example 2) (333 mg, 1.59 mmol). The reaction mixture is heated to reflux for 1 h, allowed to cool to RT and concentrated in vacuo. MPLC (CH$_3$CN/H$_2$O/TFA) purification affords the title compound: ES-MS: 316.0 [M+H]$^+$; single peak at $t_R$=3.19 min (System 2).

Example 20

[4-(4-Methyl-piperazin-1-yl)-phenyl]-(5-thiophen-3-yl-thiazol-2-yl)-amine

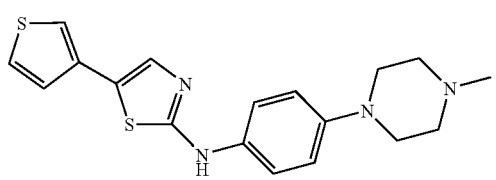

The title compound is prepared as described in Example 19 for (3-dimethylaminomethyl-phenyl)-(5-thiophen-3-yl-thiazol-2-yl)-amine but starting from [4-(4-methyl-piperazin-1-yl)-phenyl]-thiourea (Example 5). MPLC (CH$_3$CN/H$_2$O/TFA) purification affords the title compound: ES-MS: 357.1 [M+H]$^+$; single peak at $t_R$=2.82 min (System 2); $R_f$=0.59 (CH$_2$Cl$_2$/MeOH, 90/10).

Example 21

[4-(2-Diethylamino-ethoxy)-phenyl]-(5-thiophen-3-yl-thiazol-2-yl)-amine

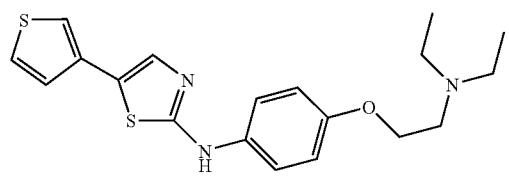

The title compound is prepared as described in Example 8 for {5-[4-(3-dimethylamino-propoxy)-phenyl]-thiazol-2-yl}phenyl-amine but starting from 4-(5-thiophen-3-yl-thiazol-2-yl-amino)-phenol (Example 12) and using (2-chloroethyl)-diethylamine hydrochloride. MPLC (CH$_3$CN/H$_2$O/TFA) purification affords the title compound: ES-MS: 374.0 [M+H]$^+$; single peak at $t_R$=3.04 min (System 2).

Example 22

{4-[2-(1-Methyl-pyrrolidin-2-yl)-ethoxy]-phenyl}-(5-thiophen-3-yl-thiazol-2-yl)-amine

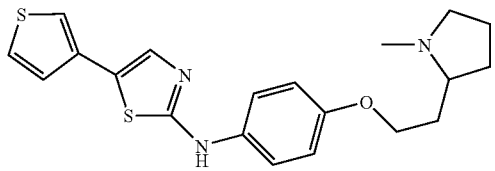

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-yl-amino)-phenol (Example 12) and using 2-(2-chloroethyl)-1-methylpyrrolidine hydrochloride. MPLC (CH$_3$CN/H$_2$O/TFA) purification affords the title compound: ES-MS: 386.0 [M+H]$^+$; single peak at t$_R$=3.09 min (System 2).

Example 23

[5-(3-Bromo-phenyl)-thiazol-2-yl]-[4-(2-diethylamino-ethoxy)-phenyl]-amine

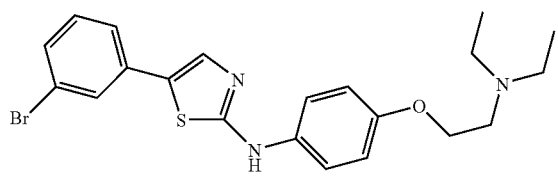

The title compound is prepared as described in Example 8 for {5-[4-(3-dimethylamino-propoxy)-phenyl]-thiazol-2-yl}-phenyl-amine but starting from 4-[5-(3-bromo-phenyl)-thiazol-2-ylamino]-phenol and using (2-chloroethyl)-diethylamine hydrochloride. After stirring the reaction mixture for 30 min at 70° C., purification of the crude material by silica gel column chromatography (CH$_2$Cl$_2$/MeOH, 95/5 then 90/10) affords the title compound: ES-MS: 447.9 [M+2]$^+$; single peak at t$_R$=3.77 min (System 2); R$_f$=0.14 (CH$_2$Cl$_2$/MeOH, 90/10).

4-[5-(3-Bromo-phenyl)-thiazol-2-ylamino]-phenol

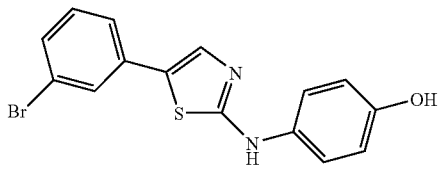

The title compound is prepared as described in Example 12 (Procedure B) for 4-(5-thiophen-3-yl-thiazol-2-yl-amino)-phenol but starting from (3-bromophenyl)-acetaldehyde. The title compound: ES-MS: 348.9 [M+2]$^+$; single peak at t$_R$=3.92 min (System 2); R$_f$=0.47 (CH$_2$Cl$_2$/MeOH, 90/10).

(3-Bromophenyl)-acetaldehyde

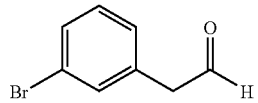

The title compound is prepared as described in Example 12 (Procedure B) for 3-thiophenylacetaldehyde but using 3-bromophenyl-ethanol. The title compound: ES-MS: 196.9 [M-2]$^-$; single peak at t$_R$=3.89 min (System 2); R$_f$=0.66 (CH$_2$Cl$_2$/Et$_2$O, 95/5).

Example 24

[5-(2-Chloro-phenyl)-thiazol-2-yl]-[4-(2-diethylamino-ethoxy)-phenyl]-amine

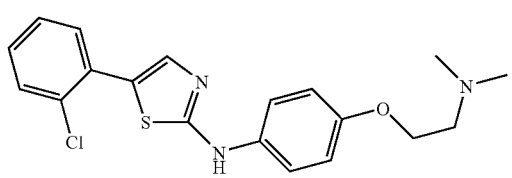

The title compound is prepared as described in Example 8 for {5-[4-(3-dimethylamino-propoxy)-phenyl]-thiazol-2-yl}-phenyl-amine but starting from 4-[5-(2-chloro-phenyl)-thiazol-2-ylamino]-phenol and using (2-chloroethyl)-dimethylamine hydrochloride. The title compound: ES-MS: 374.0 [M+H]$^+$; single peak at t$_R$=3.17 min (System 2); R$_f$=0.23 (CH$_2$Cl$_2$/MeOH, 90/10).

4-[5-(2-Chloro-phenyl)-thiazol-2-ylamino]-phenol

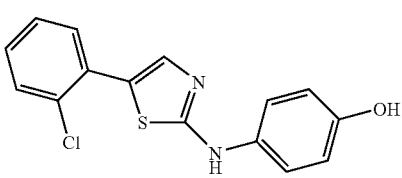

The title compound is prepared as described in Example 12 (Procedure B) for 4-(5-thiophen-3-yl-thiazol-2-yl-amino)-phenol but starting from (2-chlorophenyl)-acetaldehyde. The title compound: ES-MS: 303.0 [M+H]$^+$; single peak at t$_R$=3.59 min (System 2); R$_f$=0.21 (CH$_2$Cl$_2$/MeOH, 95/5).

31

(2-Chlorophenyl)-acetaldehyde

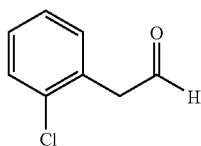

The title compound is prepared as described in Example 12 (Procedure B) for 3-thiophenylacetaldehyde but using 2-chlorophenyl-ethanol. The title compound: ES-MS: 152.9 [M−H]$^-$; single peak at $t_R$=3.82 min (System 2); $R_f$=0.70 (CH$_2$Cl$_2$/Et$_2$O, 95/5).

Example 25

[4-(4-Methyl-piperazin-1-yl)-phenyl]-[5-(3-thiophen-3-yl-phenyl)-thiazol-2-yl]-amine

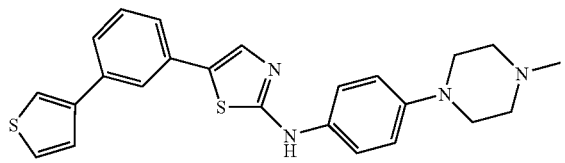

The title compound is prepared as described in Example 1 for (5-phenyl-thiazol-2-yl)-[4-(2-pyrrolidin-1-yl-ethoxy)-phenyl]-amine but using (3-thiophen-3-yl-phenyl)-acetaldehyde and [4-(4-methyl-piperazin-1-yl)-phenyl]-thiourea (Example 5). MPLC (CH$_3$CN/H$_2$O/TFA) purification affords the title compound: ES-MS: 435.0 [M+3]$^+$; single peak at $t_R$=3.09 min (System 2); $R_f$=0.25 (CH$_2$Cl$_2$/MeOH, 90/10).

(3-Thiophen-3-yl-phenyl)-acetaldehyde

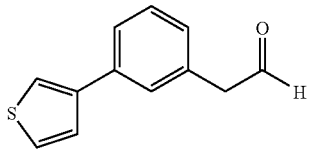

The title compound is prepared as described in Example 12 (Procedure B) for 3-thiophenylacetaldehyde but using 2-(3-thiophen-3-yl-phenyl)-ethanol. The title compound: ES-MS: 200.9 [M−H]$^-$; single peak at $t_R$=4.53 min (System 2); $R_f$=0.63 (CH$_2$Cl$_2$/Et$_2$O, 95/5).

32

2-(3-Thiophen-3-yl-phenyl)-ethanol

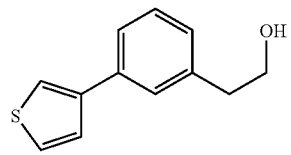

A mixture of 3-bromo-phenethyl-alcohol (1 g, 4.97 mmol), 3-thiophene-boronic-acid (1.9 g, 14.9 mmol, 3.0 equiv), Pd(PPh$_3$)$_4$ (172 mg, 0.149 mmol, 0.03 equiv), and 2M Na$_2$CO$_3$ (10.8 mL, 22.4 mmol, 4.5 equiv) in toluene (40 mL) is heated to reflux 1 h, under an argon atmosphere. The resulting suspension is allowed to cool to RT and filtered through a pad of celite, washing the filter cake with CH$_2$Cl$_2$ and water. The layers are separated. The organic phase is washed with brine, dried (Na$_2$SO$_4$), filtered and concentrated. Purification of the crude material by silica gel column chromatography (CH$_2$Cl$_2$/Et$_2$O, 95/5) affords the title compound: ES-MS: 205.0 [M+H]$^+$; single peak at $t_R$=4.27 min (System 2); $R_f$=0.32 (CH$_2$Cl$_2$/Et$_2$O, 95/5).

Example 26

[4-(2-Diethylamino-ethoxy)-phenyl]-[5-(3-thiophen-3-yl-phenyl)-thiazol-2-yl]-amine

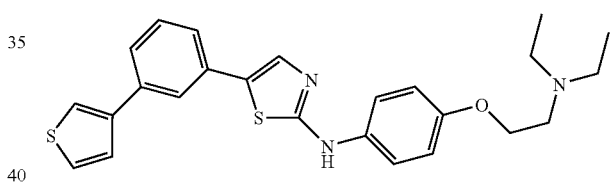

The title compound is prepared as described in Example 8 for {5-[4-(3-dimethylamino-propoxy)-phenyl]-thiazol-2-yl}-phenyl-amine but starting from 4-[5-(3-thiophen-3-yl-phenyl)-thiazol-2-ylamino]-phenol and using (2-chloroethyl)-diethylamine hydrochloride. The title compound: ES-MS: 450.0 [M+H]$^+$; single peak at $t_R$=3.98 min (System 2); $R_f$=0.14 (CH$_2$Cl$_2$/MeOH, 90/10).

4-[5-(3-Thiophen-3-yl-phenyl)-thiazol-2-ylamino]-phenol

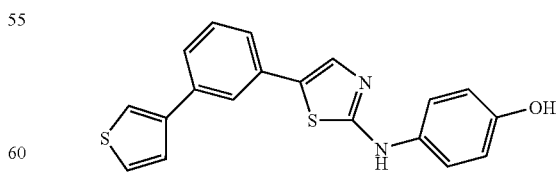

The title compound is prepared as described in Example 12 (Procedure B) for 4-(5-thiophen-3-yl-thiazol-2-yl-amino)-phenol but starting from (3-thiophen-3-yl-phenyl)-acetaldehyde (Example 25). The title compound: ES-MS: 350.9 [M+H]$^+$; single peak at $t_R$=4.16 min (System 2).

Example 27

[4-(2-Dimethylamino-ethoxy)-2-methyl-phenyl]-(5-thiophen-3-yl-thiazol-2-yl)-amine

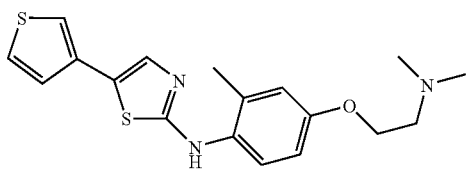

The title compound is prepared as described in Example 8 for {5-[4-(3-dimethylamino-propoxy)-phenyl]-thiazol-2-yl}-phenyl-amine but starting from 3-methyl-4-(5-thiophen-3-yl-thiazol-2-ylamino)-phenol and using (2-chloroethyl)-dimethylamine hydrochloride. The title compound: ES-MS: 360.0 [M+H]$^+$; single peak at $t_R$=2.78 min (System 2); $R_f$=0.32 (CH$_2$Cl$_2$/MeOH, 75/25).

3-Methyl-4-(5-thiophen-3-yl-thiazol-2-ylamino)-phenol

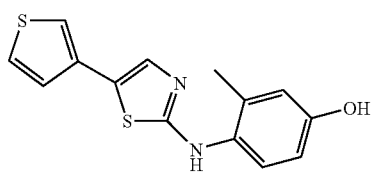

The title compound is prepared as described in Example 7 for 4-{2-[4-(2-pyrrolidin-1-yl-ethoxy)-phenylamino]-thiazol-5-yl}-phenol but starting from (4-methoxy-2-methyl-phenyl)-(5-thiophen-3-yl-thiazol-2-yl)-amine and using 4 equivalents of BBr$_3$. Title compound: ES-MS: 289.0 [M+H]$^+$; single peak at $t_R$=3.33 min (System 2); $R_f$=0.15 (CH$_2$Cl$_2$/MeOH, 95/5).

(4-Methoxy-2-methyl-phenyl)-(5-thiophen-3-yl-thiazol-2-yl)-amine

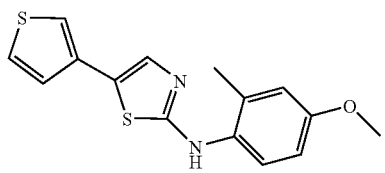

The title compound is prepared as described in Example 12 (Procedure B) for 4-(5-thiophen-3-yl-thiazol-2-yl-amino)-phenol but starting from (3-thiophen-3-yl-phenyl)-acetaldehyde (Example 25) and (4-methoxy-2-methyl-phenyl)-thiourea. The title compound: ES-MS: 303.0 [M+H]$^+$; single peak at $t_R$=3.96 min (System 2).

(4-Methoxy-2-methyl-phenyl)-thiourea

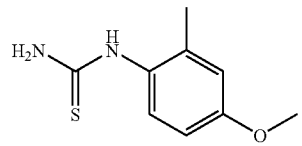

The title compound is prepared as described in Example 1 for [4-(2-pyrrolidin-1-yl-ethoxy)-phenyl]-urea but using 1-isothiocyanato-4-methoxy-2-methyl-benzene. Title compound: ES-MS: 196.9 [M+H]$^+$; single peak at $t_R$=2.46 min (System 2).

1-Isothiocyanato-4-methoxy-2-methyl-benzene

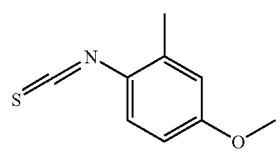

The title compound is prepared as described in Example 1 for 1-[2-(4 isothiocyanato-phenoxy)-ethyl]-pyrrolidine but using 4-methoxy-2-methylaniline. Title compound: ES-MS: 180.9 [M+H]$^+$; single peak at $t_R$=5.56 min (System 2).

Example 28

4-(3-Dimethylamino-propoxy)-2-trifluoromethyl-phenyl]-(5-thiophen-3-yl-thiazol-2-yl)-amine

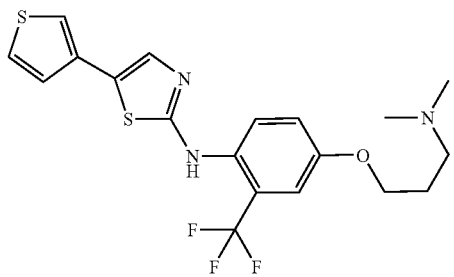

The title compound is prepared as described in Example 8 for {5-[4-(3-dimethylamino-propoxy)-phenyl]-thiazol-2-yl}phenyl-amine but starting from 4-(5-thiophen-3-yl-thiazol-2-ylamino)-3-trifluoromethyl-phenol. The title compound: ES-MS: 427.9 [M+H]$^+$; single peak at $t_R$=3:3 min (System-2); $R_f$=0.18 (CH$_2$Cl$_2$/MeOH, 90/10).

35

4-(5-Thiophen-3-yl-thiazol-2-ylamino)-3-trifluoromethyl-phenol

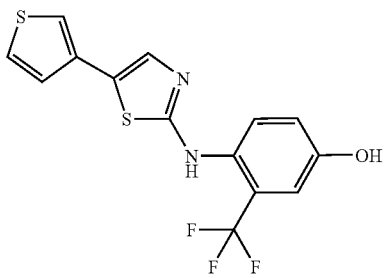

The title compound is prepared as described in Example 7 for 4-{2-[4-(2-pyrrolidin-1-yl-ethoxy)-phenylamino]-thiazol-5-yl}-phenol but starting from (4-methoxy-2-trifluoromethyl-phenyl)-(5-thiophen-3-yl-thiazol-2-yl)-amine and using 4 equivalents of BBr$_3$. Title compound: ES-MS: 342.9 [M+H]$^+$; single peak at $t_R$=3.71 min (System 2); R$_f$=0.47 (CH$_2$Cl$_2$/MeOH, 90/10).

(4-Methoxy-2-trifluoromethyl-phenyl)-(5-thiophen-3-yl-thiazol-2-yl)-amine

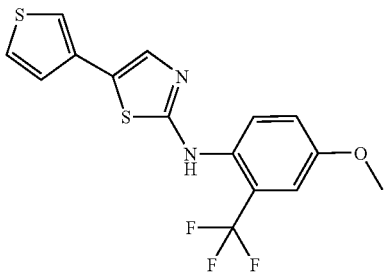

The title compound is prepared as described in Example 12 (Procedure B) for 4-(5-thiophen-3-yl-thiazol-2-yl-amino)-phenol but starting from (4-methoxy-2-trifluoromethyl-phenyl)-thiourea. After addition of the thiourea, the reaction mixture is heated to 50° C. for 30 min. The mixture is heated to 70° C. for 16 h, after addition of DIEA. The title compound: ES-MS: 357.0 [M+H]$^+$; single peak at $t_R$=4.36 min (System 2); R$_f$=0.56 (CH$_2$Cl$_2$/MeOH, 95/5).

(4-Methoxy-2-methyl-phenyl)-thiourea

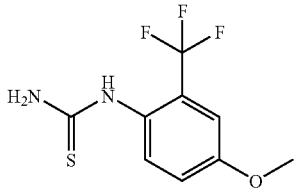

The title compound is prepared as described in Example 1 for [4-2-pyrrolidin-1-yl-ethoxy)-phenyl]-urea but using 1-isothiocyanato-4-methoxy-2-trifluoromethyl-benzene. Title compound: ES-MS: 251.0 [M+H]$^+$; single peak at $t_R$=3.13 min (System 2).

36

1-Isothiocyanato-4-methoxy-2-trifluoromethyl-benzene

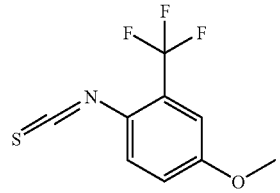

The title compound is prepared as described in Example 1 for 1-[2-(4-isothiocyanato-phenoxy)-ethyl]-pyrrolidine but using 4-methoxy-2-trifluoromethylaniline. Title compound: $^1$H NMR [400 MHz, (CD$_3$)$_2$SO]: 7.70-7.55 (m, 1H), 7.35-7.15 (m, 2H), 3.28 (s, 3H); single peak at $t_R$=5.61 min (System 2).

4-Methoxy-2-trifluoromethylaniline

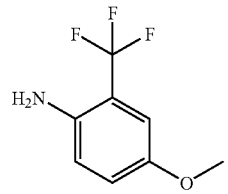

A mixture of 4-methoxy-1-nitro-2-trifluoromethyl-benzene (4.9 g, 22.2 mmol) and 5% palladium on carbon (210 mg) in EtOH (28 mL) is stirred for 2.5 h at RT, under a hydrogen atmosphere. The resulting suspension is filtered through a pad of celite. The filtrate is concentrated in vacuo to afford the title compound: ES-MS: 192.0 [M]$^+$; single peak at $t_R$=3.55 min (System 2).

4-Methoxy-1-nitro-2-trifluoromethyl-benzene

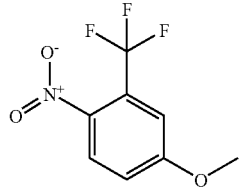

A mixture of 5-chloro-2-nitrobenzotrifluoride (5 g, 22.2 mmol) and 0.5M NaOMe (in MeOH) is stirred for 15 h at reflux. After removal of the solvent, the residue is diluted with H$_2$O (40 mL) and extracted with CH$_2$Cl$_2$ (3×150 mL). The organic phase is washed with H$_2$O (30 mL), and brine (30 mL), dried (Na$_2$SO$_4$), filtered and concentrated in vacuo to afford the title compound: ES-MS: 221.0 [M]$^-$; single peak at $t_R$=4.72 min (System 2).

Example 29

[4-(2-Dimethylamino-ethoxy)-2-trifluoromethyl-phenyl]-(5-thiophen-3-yl-thiazol-2-yl)-amine

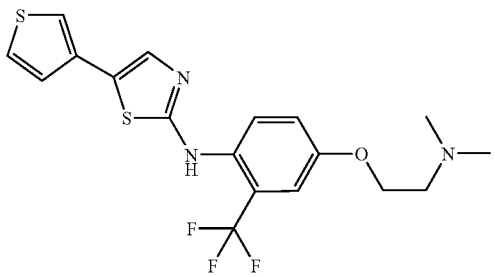

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-ylamino)-3-trifluoromethyl-phenol (Example 28) and using (2-chloroethyl)-dimethylamine hydrochloride. The title compound: ES-MS: 413.9 [M+H]$^+$; single peak at $t_R$=3.17 min (System 2); $R_f$=0.22 (CH$_2$Cl$_2$/MeOH, 90/10).

Example 30

[4-(2-Diethylamino-ethoxy)-2-trifluoromethyl-phenyl]-(5-thiophen-3-yl-thiazol-2-yl)-amine

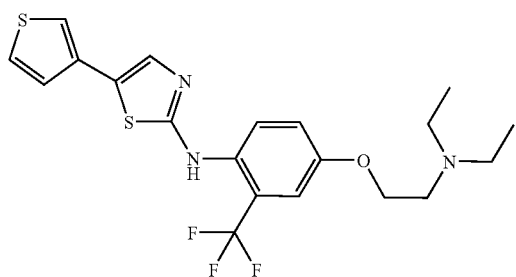

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-ylamino)-3-trifluoromethyl-phenol (Example 28) and using (2-chloroethyl)-diethylamine hydrochloride. The title compound: ES-MS: 441.9 [M+H]$^+$; single peak at $t_R$=3.41 min (System 2); $R_f$=0.25 (CH$_2$Cl$_2$/MeOH, 90/10).

Example 31

[4-(2-Diisopropylamino-ethoxy)-2-trifluoromethyl-phenyl]-(5-thiophen-3-yl-thiazol-2-yl)-amine

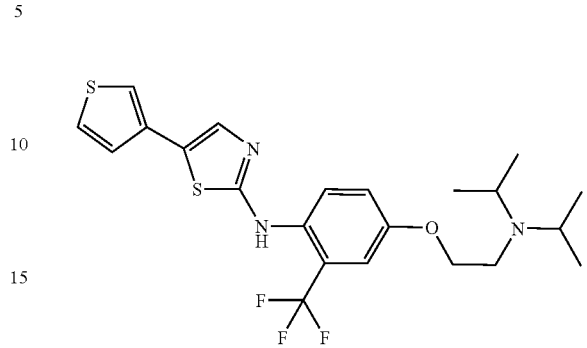

The title compound is prepared as described in Example 8 for {5-[4-(3-dimethylamino-propoxy)-phenyl]-thiazol-2-yl}phenyl-amine but starting from 4-(5-thiophen-3-yl-thiazol-2-ylamino)-3-trifluoromethyl-phenol (Example 28) and using (2-chloroethyl)-diisopropylamine hydrochloride. The title compound: ES-MS: 469.9 [M+H]$^+$; single peak at $t_R$=3.67 min (System 2); $R_f$=0.38 (CH$_2$Cl$_2$/MeOH, 90/10).

Example 32

[4-(2-Pyrrolidin-1-yl-ethoxy)-2-trifluoromethyl-phenyl]-(5-thiophen-3-yl-thiazol-2-yl)-amine

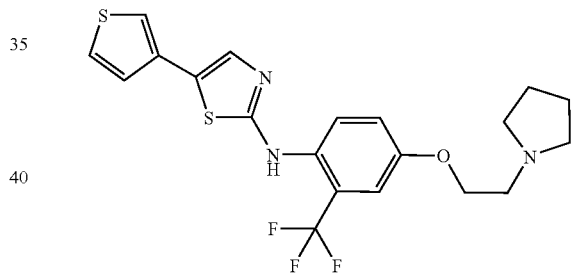

The title compound is prepared as described in Example 8 for {5-[4-(3-dimethylamino-propoxy)-phenyl]-thiazol-2-yl}-phenyl-amine but starting from 4-(5-thiophen-3-yl-thiazol-2-ylamino)-3-trifluoromethyl-phenol (Example 28) and using 1-(2-chloroethyl)-pyrrolidine hydrochloride. The title compound: ES-MS: 439.9 [M+H]$^+$; single peak at $t_R$=3.36 min (System 2); $R_f$=0.22 (CH$_2$Cl$_2$/MeOH, 90/10).

Pyrazoles

General Synthetic Scheme

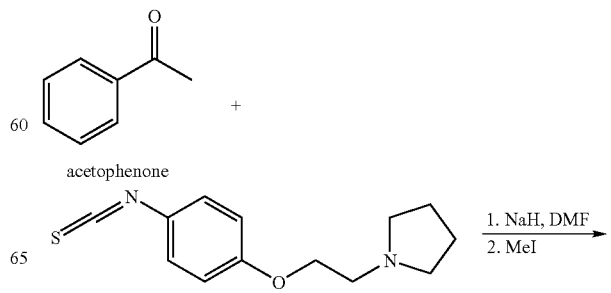

acetophenone

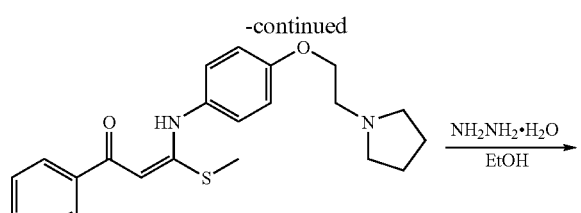

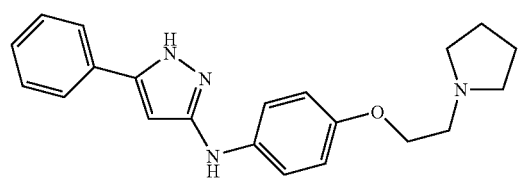

Example 33

(5-Phenyl-1H-pyrazol-3-yl)-[4-(2-pyrrolidin-1-yl-ethoxy)-phenyl]amine

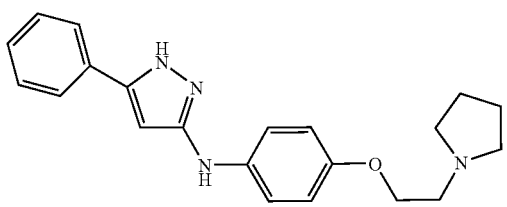

NaH (55%, 105 mg, 2.41 mmol) is added portionwise to a cold (0° C.) solution of acetophenone (285 μL, 2.41 mmol) in DMF (3 mL). The cold bath is removed and a solution of 1-[2-(4-isothiocyanato-phenoxy)-ethyl]-pyrrolidine (see intermediate of Example 1) (600 mg, 2.41 mmol) in DMF (1 mL) is added dropwise to the reaction flask. The resulting dark mixture is stirred at RT for 3 h. CH$_3$I (153 μL, 2.41 mmol) is added. The reaction mixture is allowed to stir for additional 3 h and then poured in cold (0-5° C.) water. The product is extracted in CH$_2$Cl$_2$. The organic phase is dried (Na$_2$SO$_4$), filtered and concentrated in vacuo. Purification of the crude material by silica gel (100 g) column chromatography (CH$_2$Cl$_2$/MeOH, 95/5→90/10) affords 197 mg of impure 3-methylsulfanyl-1-phenyl-3-[4-(2-pyrrolidin-1-yl-ethoxy)-phenylamino]-propenone. A mixture of the impure propenone (197 mg, 0.517 mmol) and hydrazine monohydrate (38 μL, 0.775 mmol, 1.5 equiv) in EtOH (1.6 mL) is heated to 80° C. for 17 h in a sealed tube, under an argon atmosphere. After cooling, the reaction mixture is concentrated in vacuo. The residue is purified by preparative HPLC (CH$_3$CN/H$_2$O/TFA) to provide the title compound: ES-MS: 349.1 [M+H]$^+$; single peak at t$_R$=6.11 min (System 1).

Example 34

[4-(2-Pyrrolidin-1-yl-ethoxy)-phenyl]-(5-thiophen-3-yl-1H-pyrazol-3-yl)-amine

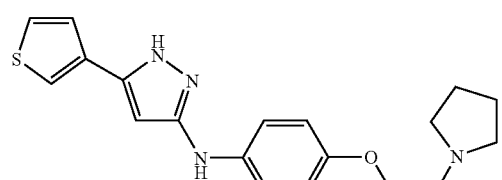

The title compound is prepared as described in Example 33 but using 3-acetylthiophene. Title compound: ES-MS: 355.0 [M+H]$^+$; single peak at t$_R$=5.93 min (System 1).

Example 35

[4-(2-Dimethylamino-ethoxy)-phenyl]-(5-thiophen-3-yl-1H-pyrazol-3-yl)-amine

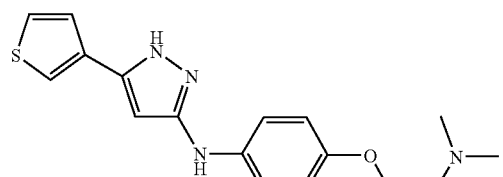

The title compound is prepared as described in Example 33 but using 3-acetylthiophene and [2-(4 isothiocyanato-phenoxy)-ethyl]-dimethyl-amine (Example 6). Title compound: ES-MS: 329.1 [M+H]$^+$; single peak at t$_R$=5.57 min (System 1).

Example 36

[4-(3-Dimethylamino-propoxy)-phenyl]-(5-thiophen-3-yl-1H-pyrazol-3-yl)-amine

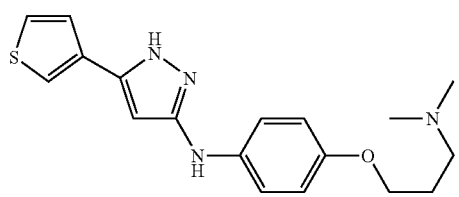

The title compound is prepared as described in Example 33 but using 3-acetylthiophene and [3-(4-isothiocyanato-phenoxy)-propyl]-dimethyl-amine. Title compound: ES-MS: 343.1 [M+H]$^+$; single peak at t$_R$=5.76 min (System 1).

[3-(4-Isothiocyanato-phenoxy)-propyl]-dimethyl-amine

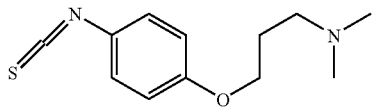

The title compound is prepared as described in Example 1 for 1-[2-(4 isothiocyanato-phenoxy)-ethyl]-pyrrolidine but using 4-(3-dimethylamino-propoxy)-phenylamine. Title compound: ES-MS: 237.1 [M+H]$^+$; single peak at $t_R$=6.91 min (System 1).

4-(3-Dimethylamino-propoxy)-phenylamine

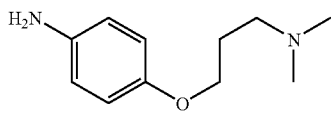

The title compound is prepared as described in Example 1 for 4-(2-pyrrolidin-1-yl-ethoxy)-phenylamine but using 1-chloro-3-dimethylamino-propane hydrochloride. After a 1.3 h stirring at 75° C. (oil bath temperature) and usual work-up, purification of the crude material by silica gel (157 g) column chromatography (CH$_2$Cl$_2$/MeOH, 50/50) provides the title compound as a dark brown oil: ES-MS: 195.0 [M+H]$^+$; R$_f$=0.13 (CH$_2$Cl$_2$/EtOH, 50/50).

Example 37

[4-(2-Diethylamino-ethoxy)-phenyl]-(5-thiophen-3-yl-1H-pyrazol-3-yl)-amine

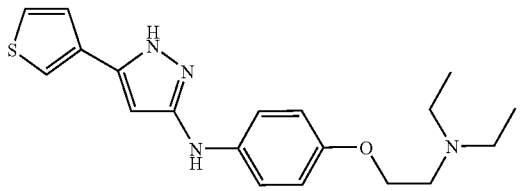

The title compound is prepared as described in Example 33 but using 3-acetylthiophene and diethyl-[2-(4-isothiocyanato-phenoxy)-ethyl]-amine. Title compound: ES-MS: 357.1 [M+H]$^+$; single peak at $t_R$=5.94 min (System 1).

Diethyl-[2-(4-isothiocyanato-phenoxy)-ethyl]-amine

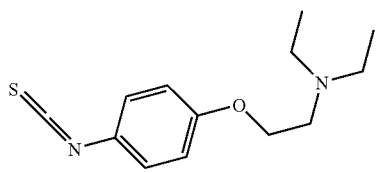

The title compound is prepared as described in Example 1 for 1-[2-(4-isothiocyanato-phenoxy)-ethyl]-pyrrolidine but using 4-(2-diethylamino-ethoxy)-phenylamine. Title compound: ES-MS: 251.1 [M+H]$^+$; single peak at $t_R$=6.99 min (System 1).

4-(2-Diethylamino-ethoxy)-phenylamine

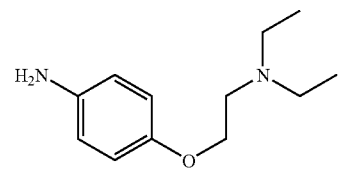

The title compound is prepared as described in Example 1 for 4-(2-pyrrolidin-1-yl-ethoxy)-phenylamine but using (2-chloro-ethyl)-diethyl-amine hydrochloride. After a 1 h stirring at RT and usual work-up, purification of the crude material by silica gel (179 g) column chromatography (CH$_2$Cl$_2$/MeOH, 80/20→70/30) affords the title compound as a dark brown oil: ES-MS: 209.2 [M+H]$^+$; R$_f$=0.21 (CH$_2$Cl$_2$/MeOH, 70/30).

Example 38

[5-(2-Chloro-phenyl)-1H-pyrazol-3-yl]-phenyl-amine

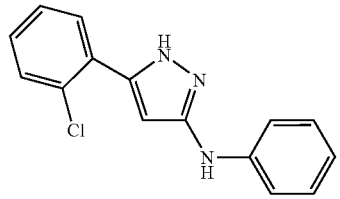

The title compound is prepared as described in Example 33 but using 2-chloroacetophenone and phenyl-isothiocyanate. Title compound: ES-MS: 270.0 [M+H]$^+$; single peak at $t_R$=7.90 min (System 3).

Example 39

[5-(2-Chloro-phenyl)-1H-pyrazol-3-yl]-[4-(4-methyl-piperazin-1-yl)-phenyl]-amine

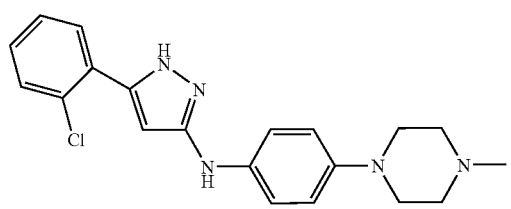

The title compound is prepared as described in Example 33 but using 2-chloroacetophenone and 1-(4-isothiocyanato-phenyl)-4-methyl-piperazine (Example 5). Title compound: ES-MS: 368.1 [M+H]$^+$; single peak at $t_R$=5.50 min (System 3).

Example 40

[4-(2-Diethylamino-ethoxy)-phenyl]-(5-thiophen-2-yl-1H-pyrazol-3-yl)-amine

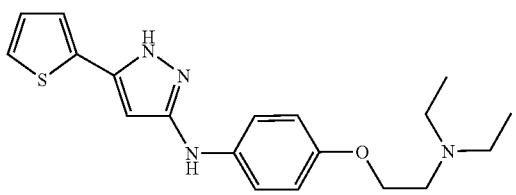

The title compound is prepared as described in Example 33 but using 2-acetylthiophene and diethyl-[2-(4-isothiocyanato-phenoxy)-ethyl]-amine (Example 37). Title compound: ES-MS: 357.1 [M+H]$^+$; single peak at $t_R$=2.98 min (System 2); $R_f$=0.11 (CH$_2$Cl$_2$/MeOH, 80/20).

Example 41

Tablets Comprising Compounds of the Formula I

Tablets, comprising, as active ingredient, 100 mg of any one of the compounds of formula I of Examples 1 to 40 are prepared with the following composition, following standard procedures:

| Composition | |
|---|---|
| Active Ingredient | 100 mg |
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, Stempeldurchmesser 10 mm).

Avicel is microcrystalline cellulose (FMC, Philadelphia, USA).

PVPPXL is polyvinylpolypyrrolidone, cross-linked (BASF, Germany).

Aerosil is silicium dioxide (Degussa, Germany).

Example 42

Capsules

Capsules, comprising, as active ingredient, 100 mg of any one of the compounds of formula I given in Examples 1 to 40, of the following composition are prepared according to standard procedures:

| Composition | |
|---|---|
| Active Ingredient | 100 mg |
| Avicel | 200 mg |
| PVPPXL | 15 mg |
| Aerosil | 2 mg |
| magnesium stearate | 1.5 mg |
| | 318.5 mg |

Manufacturing is done by mixing the components and filling them into hard gelatine capsules, size 1.

Example 43

Inhibition of the Protein Tyrosine Kinase Activity of Flt-3

The inhibition tests are carried out as described above. The IC$_{50}$ values for some of the compounds of formula I are given below:

| Compound from Example No. | Flt-3 IC$_{50}$ [μM] |
|---|---|
| 1 | 0.041 |
| 5 | 0.024 |
| 7 | 0.035 |
| 12 | 0.034 |
| 16 | 0.022 |
| 34 | 0.082 |
| 37 | 0.031 |

What is claimed is:

1. A compound of formula I

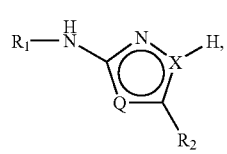

wherein
Q is S and X is C, or
Q is CH and X is N;
R$_1$ is unsubstituted or substituted phenyl; and
R$_2$ is thiophenyl or phenyl that is optionally substituted by halo, hydroxy, lower alkoxy or N,N-di-lower alkylamino-lower alkoxy;
or a salt thereof.

2. A compound of formula I according to claim 1 wherein
Q is S and X is C, or
Q is CH and X is N;
R$_1$ is phenyl that is optionally substituted by hydroxy, lower alkoxy, pyrrolidinyl-lower alkoxy, piperidinyl-lower alkoxy, morpholinyl-lower alkoxy, N,N-di-lower alkylamino-lower alkyl, N,N-di-lower alkylamino-lower alkoxy or lower alkyl-piperazinyl; and
R$_2$ is thiophenyl or phenyl that is optionally substituted by halo, hydroxy, lower alkoxy or N,N-di-lower alkylamino-lower alkoxy;
or a salt thereof.

3. A compound of formula I according to claim 1, wherein
Q is S and X is C, or
Q is CH and X is N;

R₁ is phenyl that is optionally substituted by one or more radicals selected from the group consisting of hydroxy, lower alkyl, lower alkoxy, pyrrolidinyl-lower alkoxy wherein the pyrrolidinyl moiety is optionally substituted by lower alkyl, piperidinyl-lower alkoxy, morpholinyl-lower alkoxy, N,N-di-lower alkylamino-lower alkyl, N,N-di-lower alkylamino-lower alkoxy, and lower alkyl-piperazinyl; and R₂ is thiophenyl or phenyl that is optionally substituted by halo, hydroxy, lower alkoxy, or N,N-di-lower alkylamino-lower alkoxy;

or a salt thereof.

4. A compound of formula I according to claim 1, selected from the group consisting of (5-phenyl-thiazol-2-yl)-[4-(2-pyrrolidin-1-yl-ethoxy)-phenyl]-amine;

(3-dimethylaminomethyl-phenyl)-(5-phenyl-thiazol-2-yl)-amine;

[5-(4-methoxy-phenyl)-thiazol-2-yl]-[4-(2-pyrrolidin-1-yl-ethoxy)-phenyl]-amine;

(4-methoxy-phenyl)-[5-(4-methoxy-phenyl)-thiazol-2-yl]-amine;

[5-(4-methoxy-phenyl)-thiazol-2-yl]-[4-(4-methyl-piperazin-1-yl)-phenyl]-amine;

[4-(2-dimethylamino-ethoxy)-phenyl]-[5-(4-methoxy-phenyl)thiazol-2-yl]-amine;

4-{2-[4-(2-pyrrolidin-1-yl-ethoxy)-phenylamino]-thiazol-5-yl}-phenol;

{5-[4-(3-dimethylamino-propoxy)-phenyl]-thiazol-2-yl}-phenyl-amine;

4-[5-(3-methoxy-phenyl)-thiazol-2-ylamino]-phenol;

4-[5-(3-methoxy-phenyl)-thiazol-2-yl]-[4-(2-pyrrolidin-1-yl-ethoxy)-phenyl]amine;

(4-methoxy-phenyl)-(5-thiophen-3-yl-thiazol-2-yl)-amine;

4-(5-thiophen-3-yl-thiazol-2-yl-amino)-phenol;

[4-(2-dimethylamino-ethoxy)-phenyl]-(5-thiophen-3-yl-thiazol-2-yl)-amine;

[4-(3-dimethylamino-propoxy)-phenyl]-(5-thiophen-3-yl-thiazol-2-yl)-amine;

[4-(2-pyrrolidin-1-yl-ethoxy)-phenyl]-(5-thiophen-3-yl-thiazol-2-yl)-amine;

[4-(2-piperidin-1-yl-ethoxy)-phenyl]-(5-thiophen-3-yl-thiazol-2-yl)-amine;

[4-(2-diisopropylamino-ethoxy)-phenyl]-(5-thiophen-3-yl-thiazol-2-yl)-amine;

[4-(2-morpholin-4-yl-ethoxy)-phenyl]-(5-thiophen-3-yl-thiazol-2-yl)-amine;

(5-phenyl-1H-pyrazol-3-yl)-[4-(2-pyrrolidin-1-yl-ethoxy)-phenyl]amine;

[4-(2-pyrrolidin-1-yl-ethoxy)-phenyl]-(5-thiophen-3-yl-1H-pyrazol-3-yl)-amine;

[4-(2-dimethylamino-ethoxy)-phenyl]-(5-thiophen-3-yl-1H-pyrazol-3-yl)-amine;

[4-(3-dimethylamino-propoxy)-phenyl]-(5-thiophen-3-yl-1H-pyrazol-3-yl)-amine;

[4-(2-diethylamino-ethoxy)-phenyl]-(5-thiophen-3-yl-1H-pyrazol-3-yl)-amine;

[5-(2-chloro-phenyl)-1H-pyrazol-3-yl]-phenyl-amine;

[5-(2-chloro-phenyl)-1H-pyrazol-3-yl]-[4-(4-methyl-piperazin-1-yl)-phenyl]-amine;

and pharmaceutically acceptable salts of these compounds.

5. A compound of formula I according to claim 1, selected from the group consisting of (3-dimethylaminomethyl-phenyl)-(5-thiophen-3-yl-thiazol-2-yl)-amine;

[4-(4-methyl-piperazin-1-yl)-phenyl]-(5-thiophen-3-yl-thiazol-2-yl)-amine;

[4-(2-diethylamino-ethoxy)-phenyl]-(5-thiophen-3-yl-thiazol-2-yl)-amine;

{4-[2-(1-methyl-pyrrolidin-2-yl)-ethoxy]-phenyl}-(5-thiophen-3-yl-thiazol-2-yl)-amine;

4-[[3-(4-Methyl-piperazin-1-yl)-propyl]-(5-thiophen-3-yl-thiazol-2-yl)-amino]-phenol;

[5-(3-bromo-phenyl)-thiazol-2-yl]-[4-(2-diethylamino-ethoxy)-phenyl]-amine;

[5-(2-chloro-phenyl)-thiazol-2-yl]-[4-(2-diethylamino-ethoxy)-phenyl]-amine;

[4-(4-methyl-piperazin-1-yl)-phenyl]-[5-(3-thiophen-3-yl-phenyl)-thiazol-2-yl]-amine;

[4-(2-diethylamino-ethoxy)-phenyl]-[5-(3-thiophen-3-yl-phenyl)-thiazol-2-yl]-amine;

[4-(2-dimethylamino-ethoxy)-2-methyl-phenyl]-(5-thiophen-3-yl-thiazol-2-yl)-amine;

4-(3-dimethylamino-propoxy)-2-trifluoromethyl-phenyl]-(5-thiophen-3-yl-thiazol-2-yl)-amine;

[4-(2-dimethylamino-ethoxy)-2-trifluoromethyl-phenyl]-(5-thiophen-3-yl-thiazol-2-yl)-amine;

[4-(2-diethylamino-ethoxy)-2-trifluoromethyl-phenyl]-(5-thiophen-3-yl-thiazol-2-yl)-amine;

[4-(2-diisopropylamino-ethoxy)-2-trifluoromethyl-phenyl]-(5-thiophen-3-yl-thiazol-2-yl)-amine;

[4-(2-pyrrolidin-1-yl-ethoxy)-2-trifluoromethyl-phenyl]-(5-thiophen-3-yl-thiazol-2-yl)-amine;

[4-(2-diethylamino-ethoxy)-phenyl]-(5-thiophen-2-yl-1H-pyrazol-3-yl)-amine;

and pharmaceutically acceptable salts of these compounds.

6. A pharmaceutical composition comprising a compound of formula I or a pharmaceutically acceptable salt thereof according to claim 1, together with at least one pharmaceutically acceptable carrier.

* * * * *